(12) United States Patent
Najdahmadi

(10) Patent No.: US 12,029,584 B2
(45) Date of Patent: Jul. 9, 2024

(54) LIGHT-BASED MEDICAL DEVICE

(71) Applicant: Avid Najdahmadi, San Diego, CA (US)

(72) Inventor: Avid Najdahmadi, San Diego, CA (US)

( * ) Notice: Subject to any disclaimer, the term of this patent is extended or adjusted under 35 U.S.C. 154(b) by 801 days.

(21) Appl. No.: 17/061,342

(22) Filed: Oct. 1, 2020

(65) Prior Publication Data

US 2021/0093252 A1 Apr. 1, 2021

Related U.S. Application Data

(60) Provisional application No. 62/909,207, filed on Oct. 1, 2019.

(51) Int. Cl.
| | |
|---|---|
| *A61B 5/00* | (2006.01) |
| *A61B 5/01* | (2006.01) |
| *A61B 5/145* | (2006.01) |
| *A61B 5/1459* | (2006.01) |
| *A61B 17/00* | (2006.01) |

(Continued)

(52) U.S. Cl.
CPC ............ *A61B 5/4875* (2013.01); *A61B 5/01* (2013.01); *A61B 5/14546* (2013.01); *A61B 5/1459* (2013.01); *A61B 5/742* (2013.01); *A61B 17/00234* (2013.01); *A61B 17/30* (2013.01); *A61B 17/3201* (2013.01); *A61B 17/3211* (2013.01); *A61B 17/3421* (2013.01); *A61M 25/00* (2013.01); *A61M 25/104* (2013.01); *G02B 23/243* (2013.01); *A61B 2562/0266* (2013.01)

(58) Field of Classification Search
CPC ...... A61B 5/4875; A61B 5/01; A61B 5/14546; A61B 5/1459; A61B 5/742; A61B 17/00234; A61B 17/30; A61B 17/3201; A61B 17/3211; A61B 17/3421; A61B 2562/0266; A61M 25/00; A61M 25/104; G02B 23/243
See application file for complete search history.

(56) References Cited

U.S. PATENT DOCUMENTS 5,769,791 A * 6/1998 Benaron ............ A61B 17/3417
600/476
8,630,698 B2 1/2014 Fengler et al.
(Continued)

OTHER PUBLICATIONS

International Search Report and Written Opinion received in PCT/US2020/053828, dated Jan. 5, 2021 (22 pages).

*Primary Examiner* — Jonathan T Kuo
(74) *Attorney, Agent, or Firm* — Redbrick 1P, P.C.

(57) ABSTRACT

Embodiments describe a light-based medical device that uses light to luminesce tissue, and collect the reflected light, to perform analysis on the reflection characteristics in real-time to detect the type of surrounding tissue as well deeper tissue in the trajectory of the luminescence. Such device can be incorporated inside needles, catheters, tubes or piercing or biopsy tools, surgical blades, surgical tweezers, and so on, to direct their insertions and operations in specific zones. Importantly, because of the easy-to-use design, embodiments can be used without the need of highly trained personnel or expensive hospital equipment. Therefore, embodiments can be utilized in emergency situations that require fast responses, performed in ERs, moving vehicles, ambulances, and battlefields.

64 Claims, 16 Drawing Sheets

(51) Int. Cl.
*A61B 17/30* (2006.01)
*A61B 17/3201* (2006.01)
*A61B 17/3211* (2006.01)
*A61B 17/34* (2006.01)
*A61M 25/00* (2006.01)
*A61M 25/10* (2013.01)
*G02B 23/24* (2006.01)

(56) References Cited

U.S. PATENT DOCUMENTS

| | | | |
|---|---|---|---|
| 2002/0045811 A1* | 4/2002 | Kittrell | G02B 6/4296 |
| | | | 606/7 |
| 2002/0159055 A1 | 10/2002 | Bennett et al. | |
| 2006/0017920 A1 | 1/2006 | Tsuchiya et al. | |
| 2007/0015963 A1* | 1/2007 | Fengler | A61B 1/043 |
| | | | 348/E5.029 |
| 2007/0149858 A1 | 6/2007 | Ogawa et al. | |
| 2007/0156021 A1* | 7/2007 | Morse | A61B 1/0692 |
| | | | 600/176 |
| 2010/0045612 A1 | 2/2010 | Molne | |
| 2011/0230715 A1 | 9/2011 | Saito | |
| 2013/0267799 A1* | 10/2013 | Harjunmaa | G01N 33/49 |
| | | | 600/316 |
| 2014/0227437 A1* | 8/2014 | DeBoer | B29D 11/00009 |
| | | | 427/162 |
| 2015/0112132 A1 | 4/2015 | Nieman et al. | |
| 2015/0159830 A1 | 6/2015 | Joergensen | |
| 2015/0216652 A1 | 8/2015 | Jansen | |
| 2015/0260656 A1* | 9/2015 | Zilberstein | G01N 21/78 |
| | | | 356/402 |
| 2016/0022126 A1 | 1/2016 | Ramesh et al. | |
| 2018/0235438 A1 | 8/2018 | Kanamori et al. | |

* cited by examiner

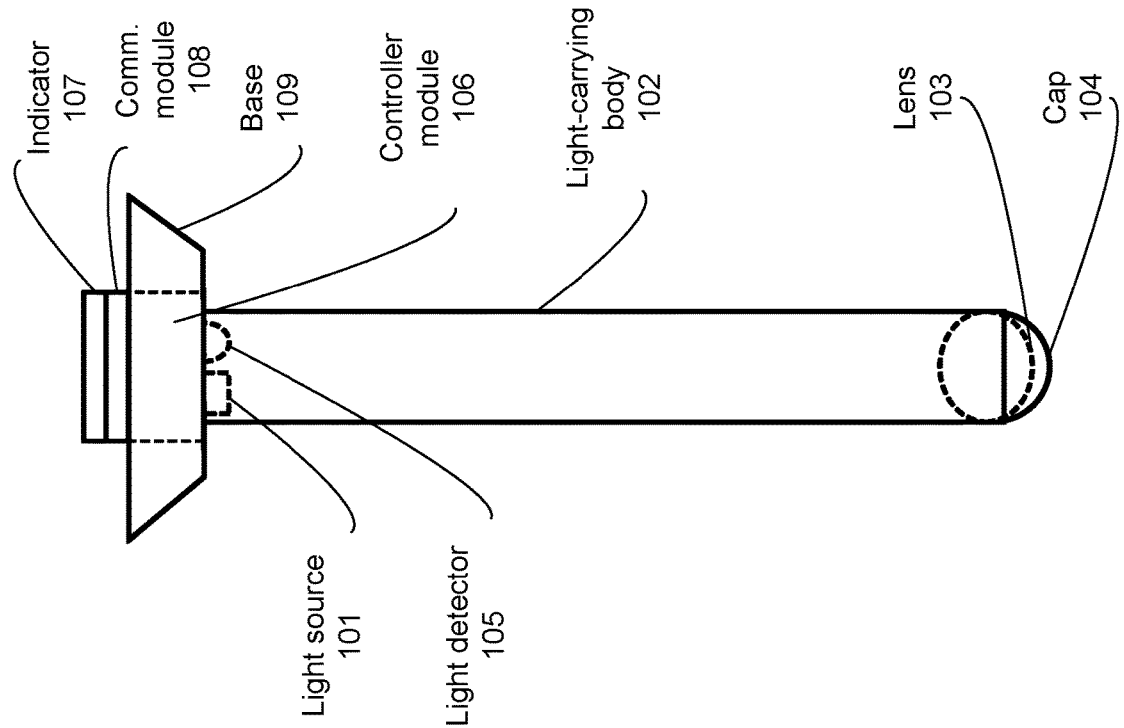
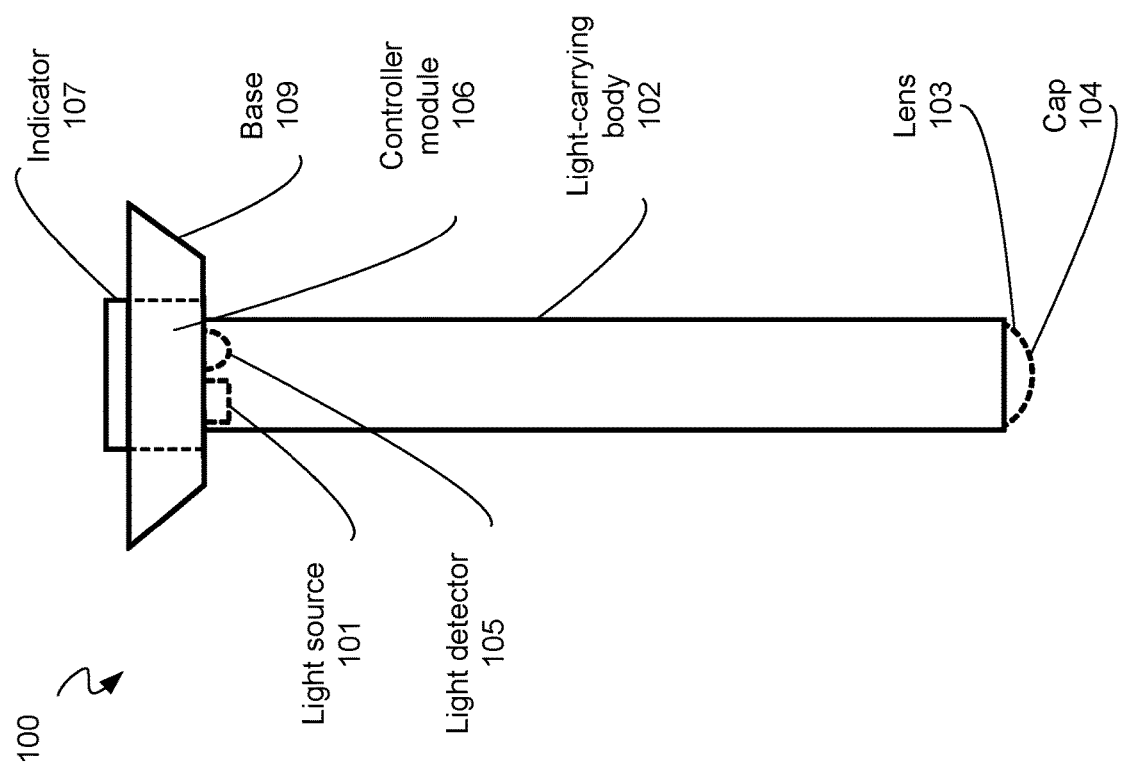

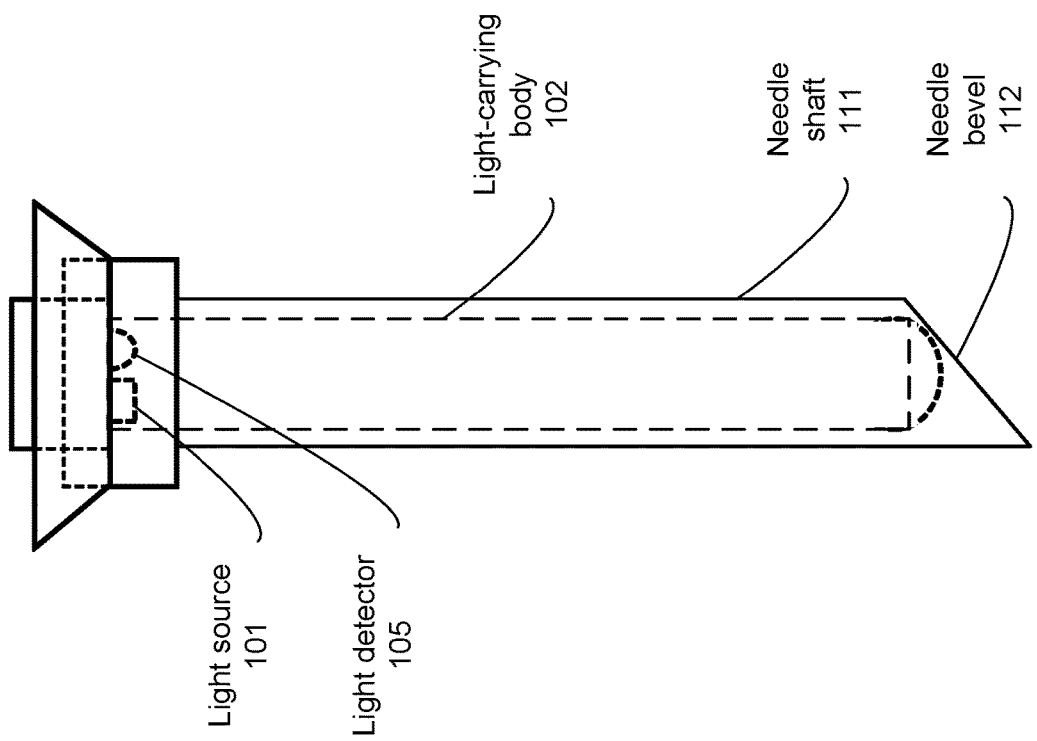
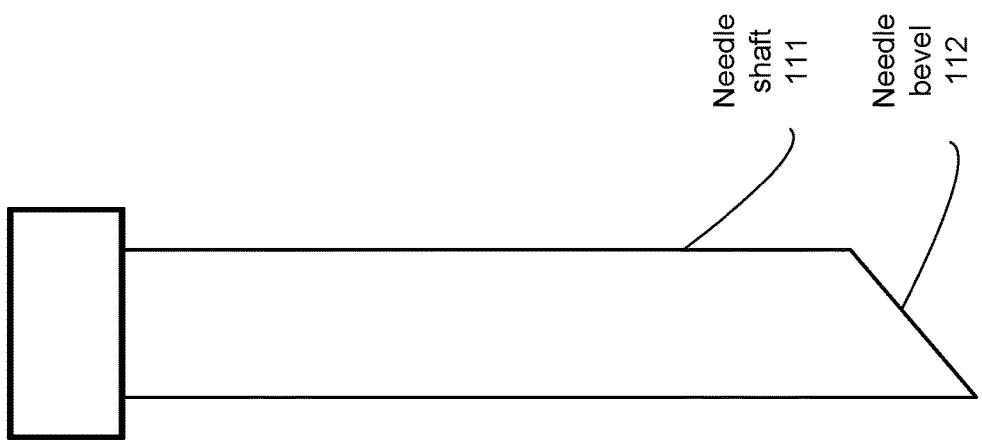

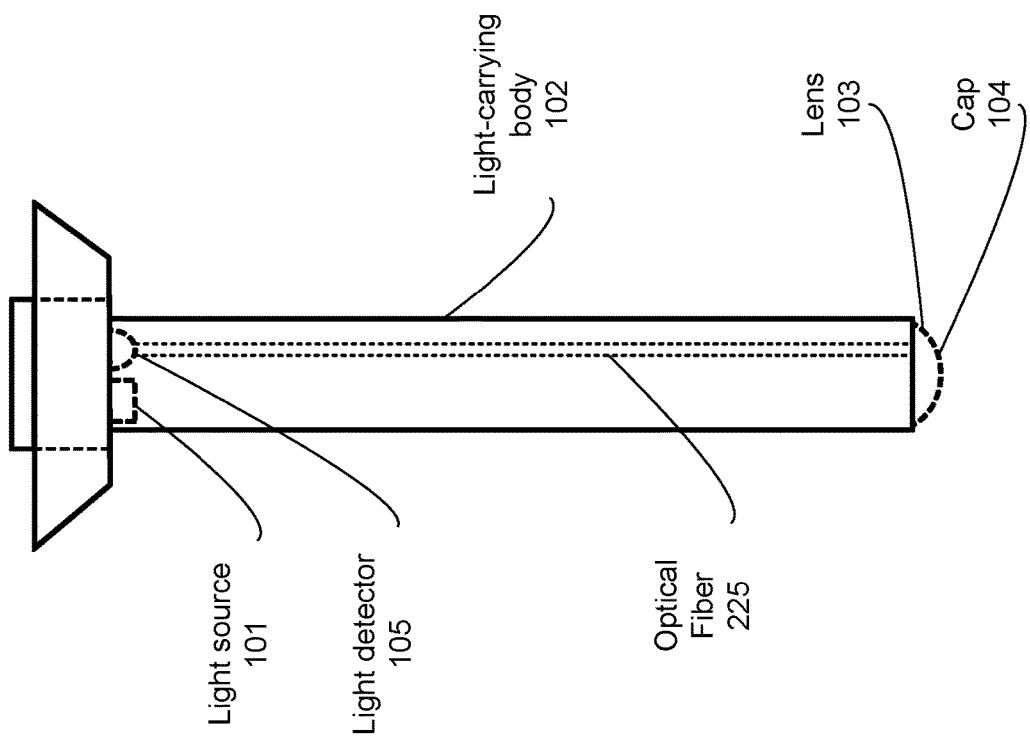
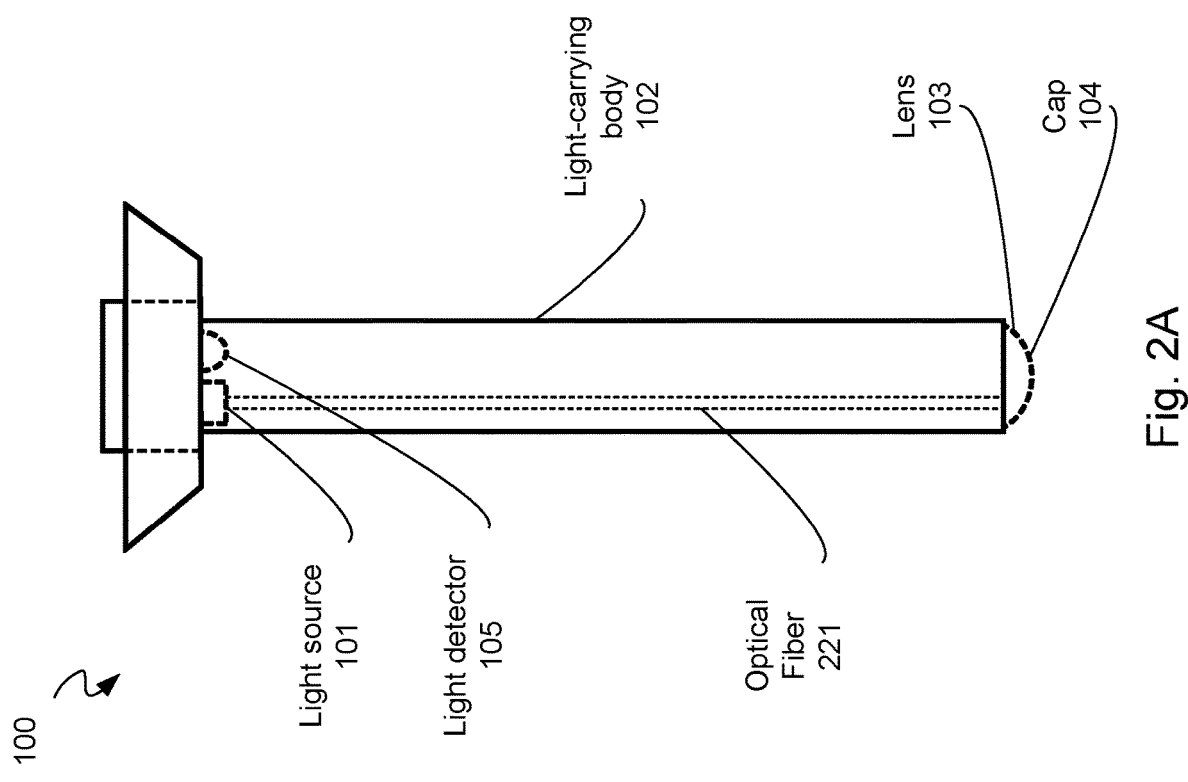

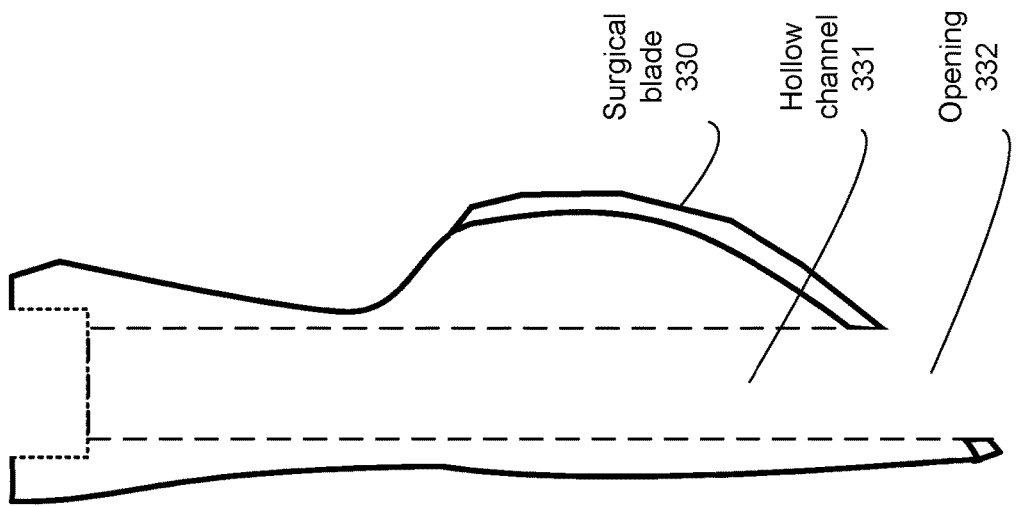
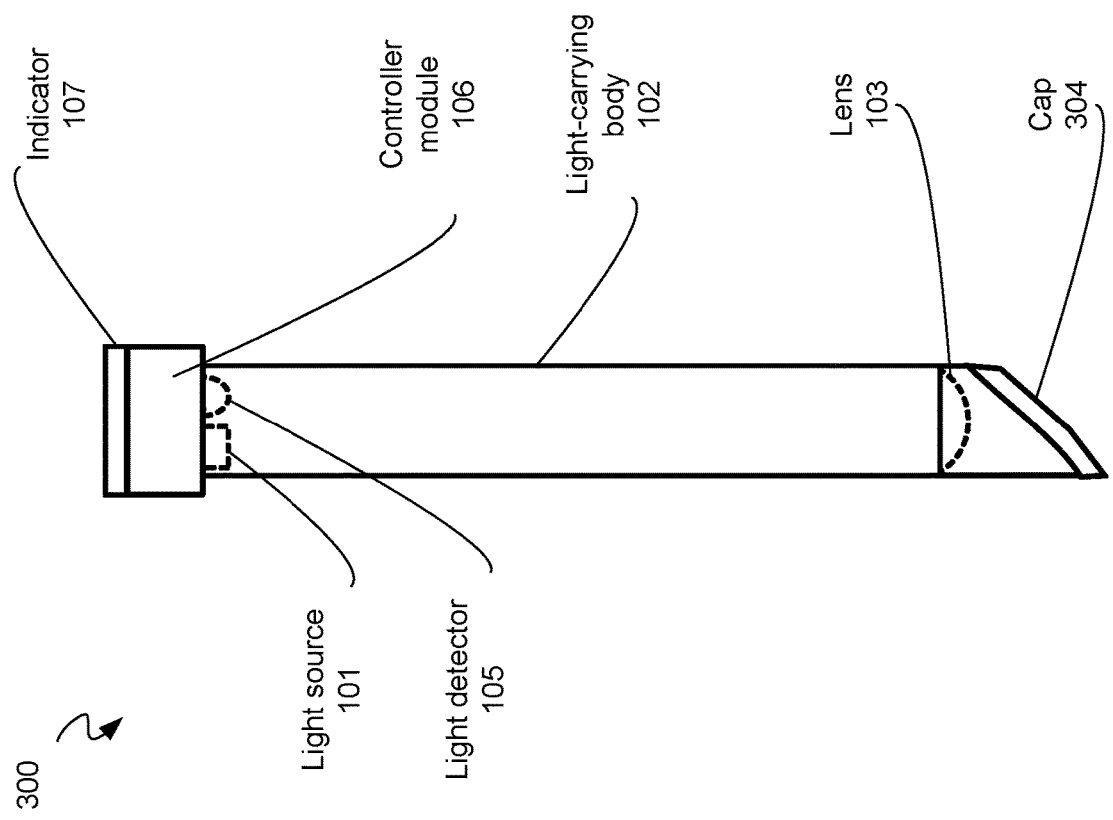

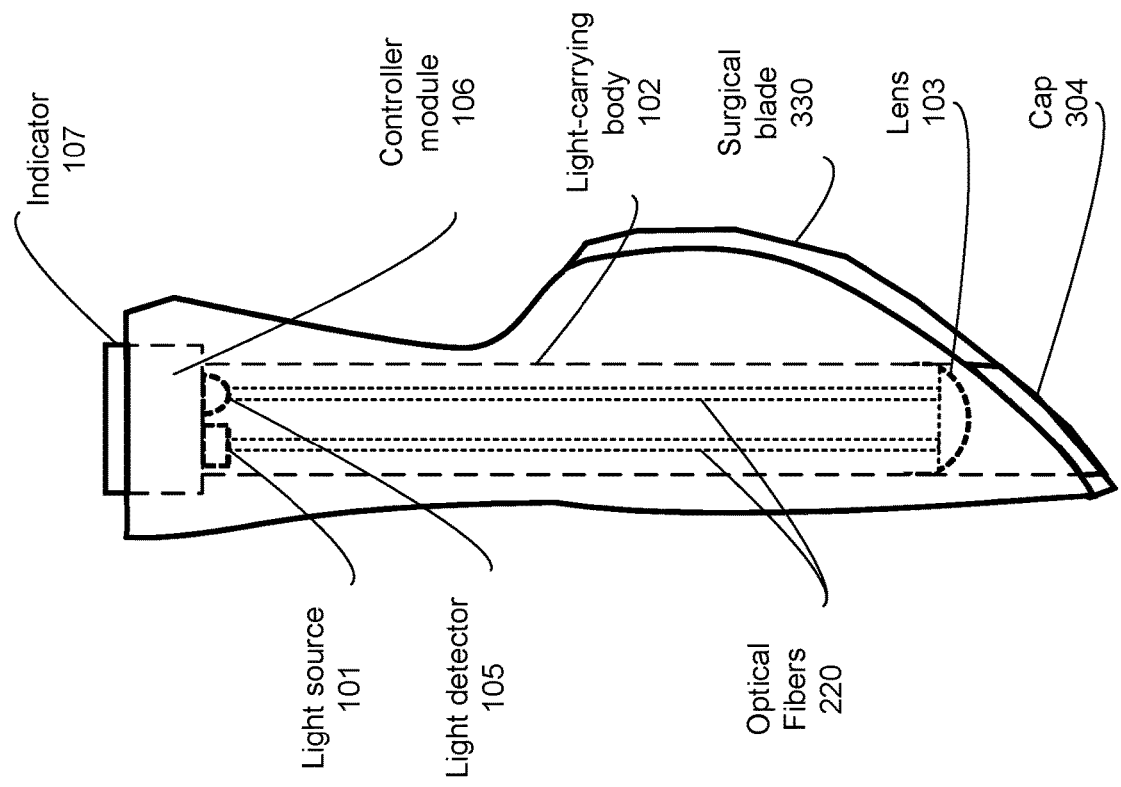
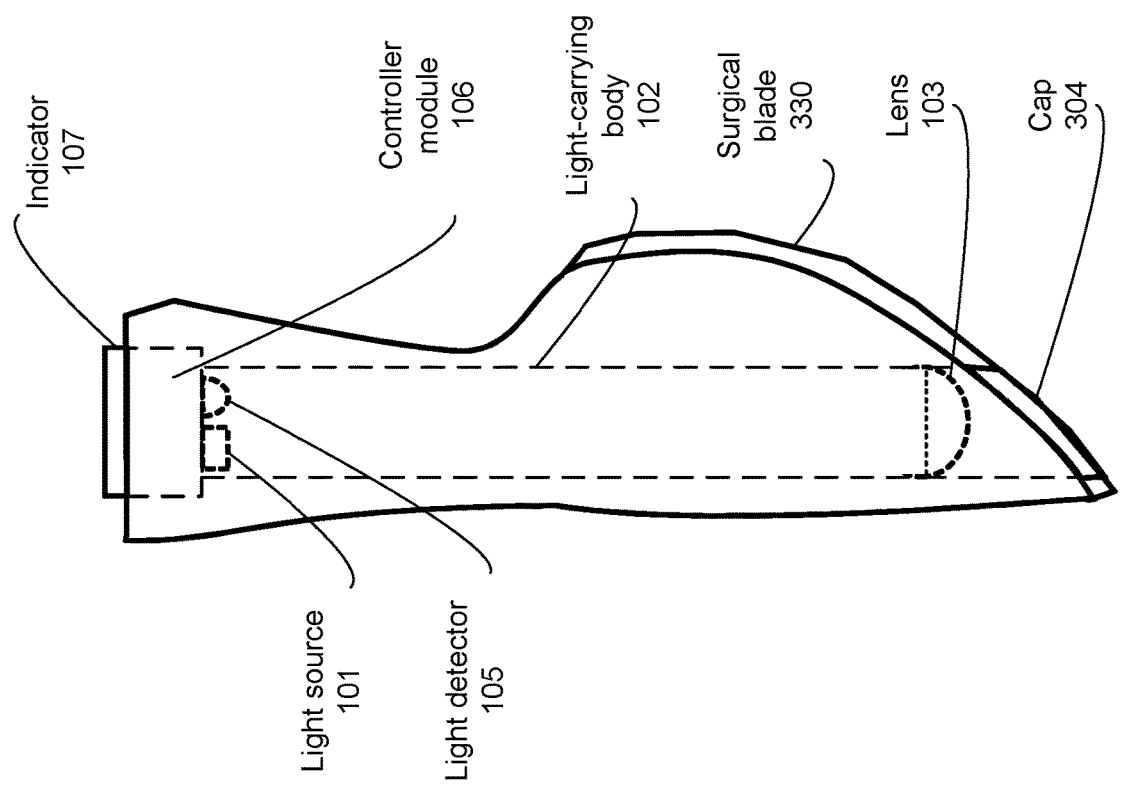
Fig. 3C
Fig. 3D

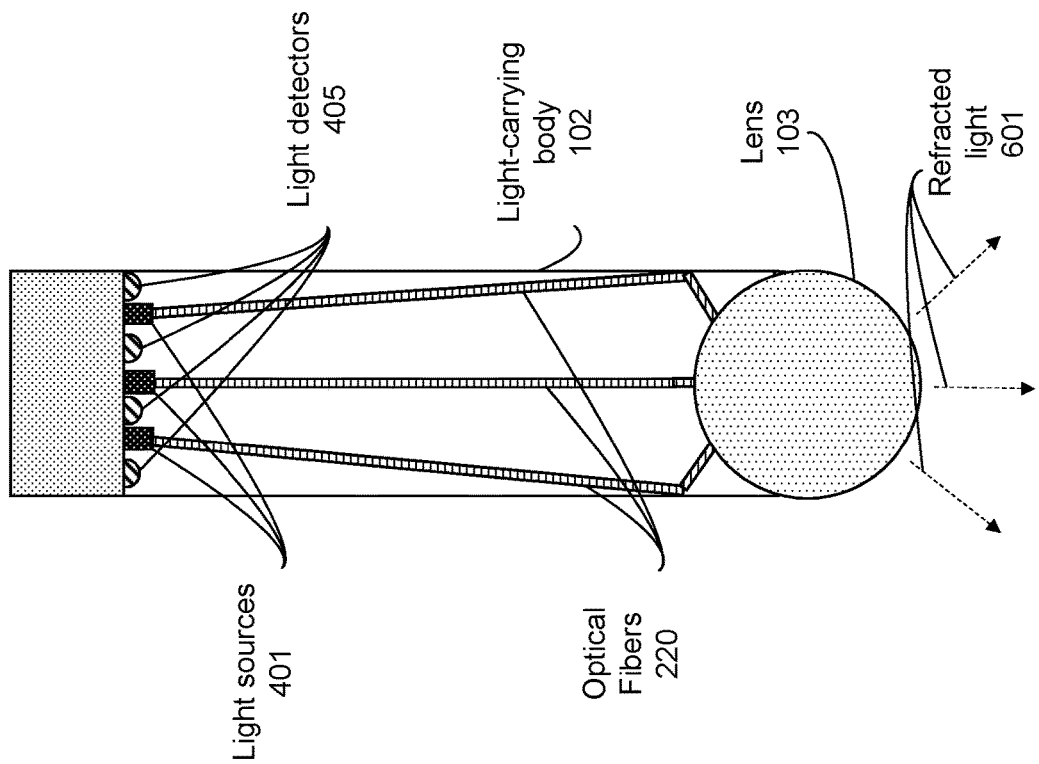
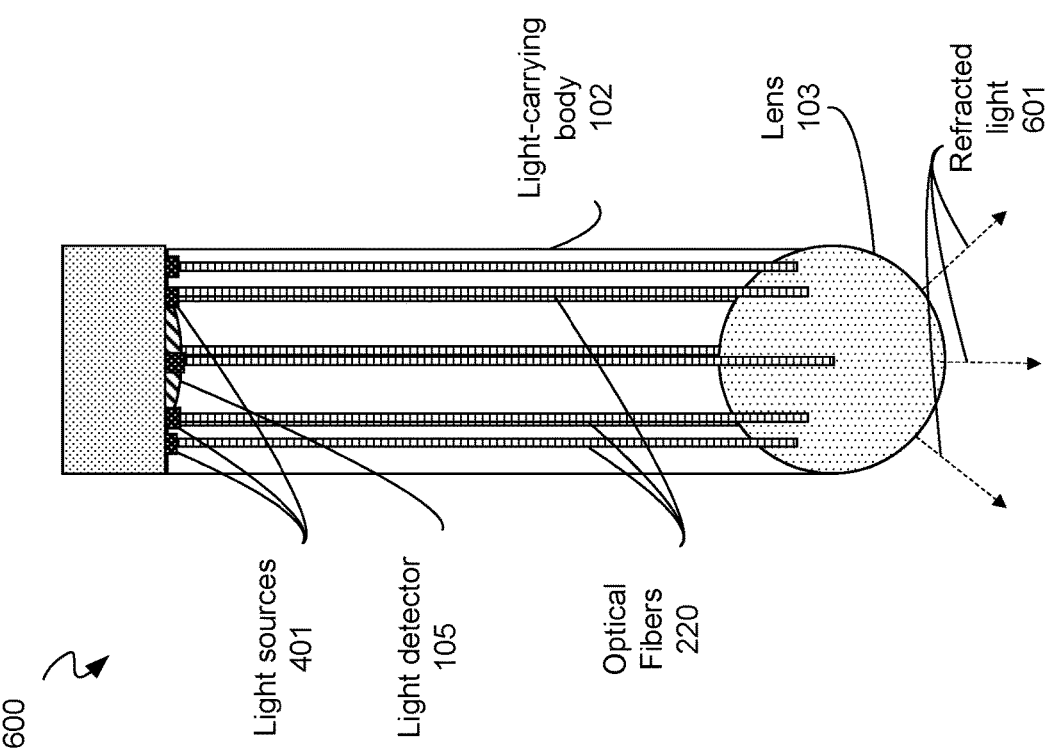
Fig. 6B
Fig. 6A

LIGHT-BASED MEDICAL DEVICE

CROSS-REFERENCE TO RELATED APPLICATIONS

This application claims the benefit of U.S. Provisional Patent Application Ser. No. 62/909,207, "Light Guided Insertion Device", filed Oct. 1, 2019, the entire disclosure of which is incorporated by reference herein, in its entirety, for all purposes.

BACKGROUND

Current techniques of precision insertions into specific anatomical zones are usually only performed by experienced medical practitioners because they can often be difficult, require medical training and practice, and require expensive hospital equipment. For example, procedures that involve the insertion of a catheter require precision and are difficult to perform. Specific examples include procedures performed during cardiac catherization or insertion of different types of dialysis catheters.

Other examples of targeted areas for insertion are vessels, arteries, or veins. For example, the insertion of a central venous catheter into an external or internal jugular vein, or the insertion of a balloon catheter to widen a narrowed or obstructed artery/vein. In another example, the insertion of a biopsy needle to collect a sample (e.g., from a lymph node). In yet another example, during local drug administration, insertion of a needle deep into tissue to deliver a certain medicine to a specific area (e.g., nerve block injection of anesthetic near the nerve/pain receptor connected to a specific nerve or joint).

An important example that often requires quick intervention and correct insertion is cricothyrotomy or tracheotomy, a procedure that involves placing a tube through an incision in the cricothyroid or trachea membrane to establish an airway for oxygenation and ventilation. Another example involves the performance of a thoracostomy. For instance, when treating a patient experiencing pneumothorax, hemothorax, hemopneumothorax, or hydrothorax, a tube is inserted from between the ribs into the pleural space to help drain air and allow the lungs to expand.

Such insertions are difficult to perform and can be dangerous because the tissue(s) in the vicinity of the inserting needle/tool can damage important vessels, cartilage, or bone tissue. Moreover, some procedures require quick and near flawless interventions (e.g., pneumothorax). For guiding such insertions, currently ultrasound guided systems or Fluoroscopy X-Ray based image processing techniques are available. However, these techniques use complicated processes, which require image processing, local anesthesia, and constant analysis of the sound waves/x-rays reflected from the tissue, thereby requiring the use of expert personnel and equipment. Consequently, based on the available technologies, performing fast insertion procedures are difficult in emergency situations (e.g., inside of a moving ambulance or in the battlefield on a wounded soldier).

Therefore, there is an unmet need for insertion devices that can be used to facilitate difficult and precise insertion procedures.

SUMMARY

Embodiments herein describe a light-based medical device capable of luminescing tissue and analyzing the collected light from the tissue, to determine the type of tissue/material and predict the type of the proximal tissue/material in the same trajectory and provide easy and quickly understandable feedback to practitioner. This light-based medical device can be incorporated into existing medical tools, such as insertion systems including but not limited to tubes, catheters, needles, biopsy punches, etc. Or it can be incorporated into surgical tools, including but not limited to surgical blades, tweezers, and surgical scissors. In addition, this light-based medical device can be incorporated and work in conjunction with other medical devices specifically designed for a certain use, including but not limited to endoscopes, trocars, and insertion devices targeted to reach airways to perform cricothyrotomy, thoracostomy and the like. In one embodiment, the light-based medical device can include (i) light sources (ii) light-carrying components (for example reflective hollow channel(s) such as optical fiber(s)), (iii) lens(es) at the tip of the device to guide and direct luminescing light to the tissue and its reflectance from the tissue back to the device, (iv) a sealing cap at the tip of the device made from a transparent material and matching the external profile of the medical tool (this cap can pass light through and block the entrance of tissue), (v) light detectors(s) to detect the collected reflectance, as well as (vi) a control module for data processing/acquisition at the back end of the device to control the light source(s) and light detectors(s) and analyze the reflected light. In some cases, the device also include an (vii) indicator that shows the type of the surrounding and/or upcoming tissue. In some embodiments, the device also contains a (iix) communication module to transmit the signal and/or analyzed data to a receiver, monitor, laptop, or computer. The spectrum and intensity of the reflection at different ranges of light wavelengths, and also traveling from different trajectories with respect the direction of the device, can be then analyzed to provide feedback about the type of the surrounding tissue, and the tissue farther away in the direction of the luminesce and/or insertion as well as other directions with respect to the insertion and/or luminescence.

Other embodiments will be apparent from the following description and the appended claims.

BRIEF DESCRIPTION OF THE DRAWINGS

Embodiments are illustrated by way of example, and not by way of limitation, in the figures of the accompanying drawings and in which like reference numerals refer to similar elements.

FIGS. 1A-1D show a light-based medical device, in accordance with one or more embodiments.

FIGS. 2A-2D show a light-based medical device, in accordance with one or more embodiments.

FIGS. 3A-3G show a light-based medical device, in accordance with one or more embodiments.

FIGS. 6A-6G show a light-based medical device, in accordance with one or more embodiments.

DETAILED DESCRIPTION

Figure 2D:
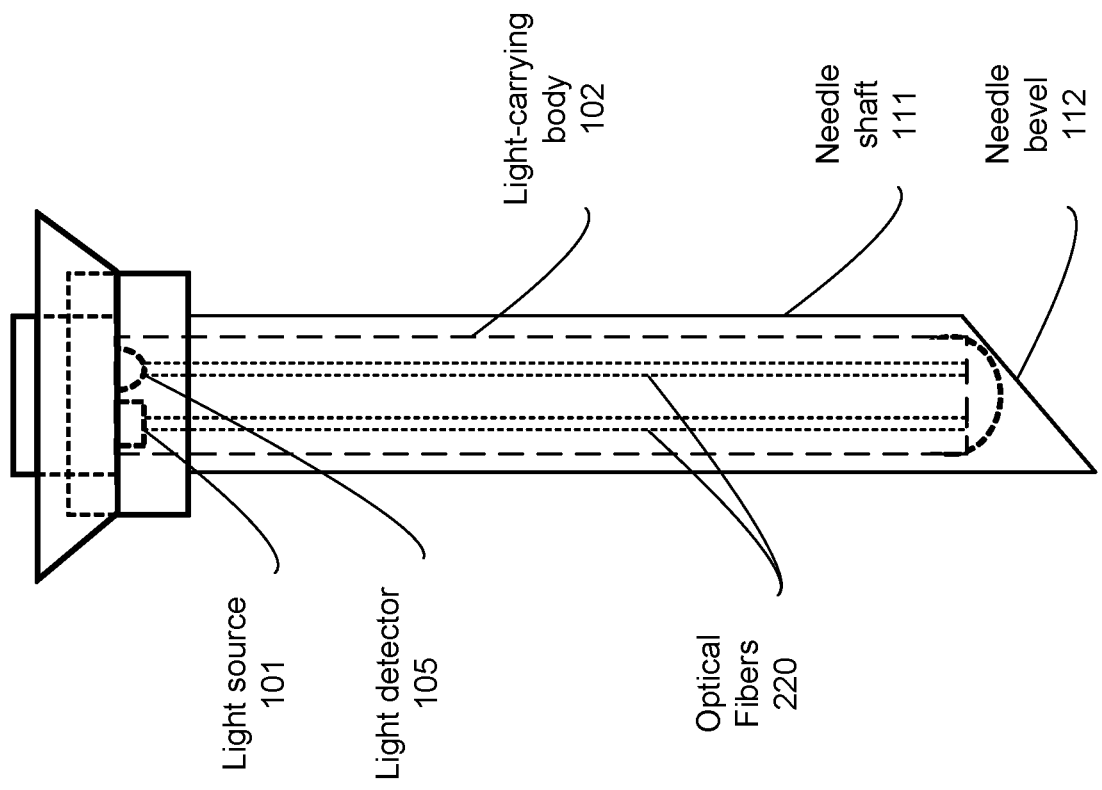

Specific embodiments will now be described in detail with reference to the accompanying figures. Like elements in the various figures are denoted by like reference numerals for consistency. In the following detailed description of embodiments, numerous specific details are set forth in order to provide a more thorough understanding of the invention. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. It will be apparent to one of ordinary skill in the art that the invention can be practiced without these specific details. In other instances, well-known features have not been described in detail to avoid unnecessarily complicating the description.

In general, embodiments of the present disclosure provide a light-based medical device capable of being used in conjunction with a multitude of medical tools (e.g., tools that cut, penetrate, or reach specific regions/points within the body). In various embodiments, the device emits/radiates light in one or more configurations (e.g., wavelength, intensity, phase, direction, coherence, polarity, combinations thereof, etc.), to illuminate media (e.g., human or animal tissue) in a surrounding area and measures the reflected (i.e., the reflectance) or passed-through light. In other words, the light received at a probe portion/end of the light-based device.

Based on an analysis of characteristics of the reflected light (e.g., wavelengths, intensities, phase, direction, coherence, polarity, combinations thereof, etc.), the device can detect the type of tissue in real-time. For example, the type of tissue immediately surrounding a portion of a medical tool (e.g., at the inserted end of the tool), the type of tissue in the general region of the medical tool (e.g., proximal to the tissue immediately surrounding the portion of a medical tool), and/or the type of superficial tissue (top/outside layer(s)) near a potential target area.

In one or more embodiments, the device can be incorporated into or implemented with existing medical tools. For example, insertion systems including but not limited to tubes, catheters, needles, biopsy punches, etc. In other examples, "sharps," which are medical devices like needles, scalpels, and other tools that cut or go into the skin. For example, surgical blades, surgical scissors, or surgical tweezers. Such medical tools are oftentimes used for cutting or targeting particular tissue (e.g. vein, artery, lymph node, fat tissue, muscle tissue, bone, tumor, etc.)/a foreign object (e.g., that needs to be removed such as bullet fragments, sutures, etc.) and require a high level of precision.

In further examples, the device can be used with medical devices designed for specific procedures. For example, endoscopes, trocars, and insertion devices targeted to reach airways (e.g., to perform procedures such as cricothyrotomy, thoracostomy, and the like).

In one or more embodiments, the device facilitates the use of medical tools by automatically detecting the types of tissue before or during penetration of the tissue, thereby providing real-time feedback to the user based on the detection to provide guidance. Such a device can be used in plethora of situations to provide quick feedback. For example, in the medical field during performance of insertions that must be performed quickly and precisely (e.g., during emergency situations in an ambulance or emergency room). Importantly, the device can simplify and quicken medical procedures that could be critical when treating a wounded soldier in the battlefield that requires quick intervention and oftentimes by fellow soldiers in non-ideal situations. An example would be performing a cricothyrotomy on a wounded soldier to clear the airway for breathing while in a moving vehicle in the battlefield.

It should be understood that in various embodiments, the light-based device may be used in conjunction with non-medical tools in non-medical applications. For example, to find, reach, or be guided to target material (e.g., where there is no clear visibility).

FIG. 1A shows a light-based medical device 100, in accordance with one or more embodiments. As shown in FIG. 1A, the device 100 includes multiple components including a light source 101, a light-carrying body 102, a lens 103, a cap 104, a light detector 105, and/or a controller module 106. It should be appreciated that the device 100 may not include some of these components (e.g., not include a cap 104), may include additional components (e.g., an indicator 107, a communication module 108, and/or a base 109), or a combination thereof (e.g., include the communication module 108 but not the indicator 107).

Turning to FIGS. 1C and 1D, the light-based device 100 may be used in conjunction with a medical implement or tool. For example, FIG. 1C shows a needle 110 (e.g., a hypodermic needle) including a needle shaft 111 and a needle bevel 112. FIG. 1D shows the device 100 located inside of the needle 110. Specifically, the light-carrying body 102 of the device 100 is located inside the needle shaft 110.

As shown, the light-carrying body 102 may extend through the needle shaft 111 such that the end of the device 100 including the lens 103 and/or cap 104 (also referred to herein as the insertion end or distal end) is located near the needle bevel 112. For example, the lens 103 may be located just behind/inside the needle bevel 112, substantially flush with the plane defined by the needle bevel 112, or just in front/outside of the needle bevel 112.

In one or more embodiments, the light-carrying body 102 is composed at least in part by a rigid material. In some embodiments, the light-carrying body 102 is composed at least in part or fully by a flexible material (e.g., a flexible polymer). In some embodiments, the inside surface of the light-carrying body 102 is at least in part composed or coated by an optically reflective material. In other embodiments, a light-carrying body 102 is not included (e.g., where fiber optic cables may be used instead).

In one or more embodiments, the device 100 remains intact during an insertion procedure involving the needle 110. The device 100 can be removed prior to an injection (e.g., local drug administration like a nerve block injection of an anesthetic near the nerve/pain receptor connected to a specific nerve or joint) or sample collection step, leaving only the needle 110 in place. In some embodiments, the device 100 can remain inside the needle 110 during an injection or sample collection step. In one example, channel(s) may be incorporated into or around the device that allow the passage of contents through the channels. In another example, the area between the device 100 and the needle 110 can accommodate the passage of contents (e.g., injection of drugs in the case of local drug administration, or removal of tissues such as cancer biopsies, infection sites, or fluids such as blood, water etc.).

Returning to FIG. 1A, in one or more embodiments, a base 109 (also referred to as a holder herein) may be coupled with various components including, for example, the light sources 101, light-carrying bodies 102, light detectors 105, controller module 106, indicators 107, and/or communication module 108.

In one or more embodiments, the light-carrying body 102 may be a reflective hollow channel. In some embodiments, the light-carrying body 102 includes one or more optical fibers. In some embodiments, the light-carrying body 102 is a fiber optic cable.

In one or more embodiments, the light-carrying body 102 is in an elongated shape (e.g., cylindrical, square-pegged, etc.). In some embodiments, the light-carrying body 102 is coated on the inside with a reflective material. Accordingly, the light-carrying body 102 can carry light to and back from tissue.

In one or more embodiments, the light source 101 may be coupled with the base 109 and/or located such that it is operable to emit light that travels along the light-carrying body 102 (guided either by the light-carrying body 102 itself or optical fiber(s) within the light-carrying body 102). In one or more embodiments, the light source 101 may be coupled with an optical fiber.

In one or more embodiments, the lens 103 may be located at the insertion end of the light-carrying body 102 (or of the device 100). The lens may guide and direct light (e.g., through refraction) emitted from the light source 101 toward the tissue and its reflectance from the tissue back toward the light detector 105. The lens 103 may be a transmissive optical component that focuses or disperses the light beam by means of refraction. The lens 103 can include a single transparent material (or at least semi-transparent), or can include several single lenses, arranged along the same common axis and/or dispersed in XYZ coordinates. Lens(es) can be in different shapes or geometries, including but not limited to biconvex (e.g., as the lens 103 depicted in FIG. 1A may be), plano-convex (e.g., as the lens 103 depicted in FIG. 1A may be), positive meniscus, plano-concave, biconcave, spherical (e.g., as the lens 103 depicted in FIG. 1B may be), or combination thereof to create compound lenses. Lens can be made from different types of materials including but not limited to polymers, ceramics, metals, etc. Some non-limiting examples of materials that can be used to make lens(es) include polyamide, silicone, nylon, PDMS, polycarbonate, carbon, industrial glass, sapphire, single or poly-crystalline transparent ceramics such Al2O3, yttria alumina garnet (YAG), neodymium-doped Nd:YAG, fused silica, various fluorides, BaF2, MgF2, Lif, ZnS, CsBr Csi, semiconductors like silicon, germanium and gallium arsenide, or other composites.

In some embodiments, the lens 103 is coupled with an optical fiber. The lens may be transparent or at least semi-transparent (e.g., 1-100% transparent as opposed to 0% or completely opaque). In some embodiments, the lens may be coated or made with light-filtering material operable to filter specific wavelengths.

In some embodiments, the lens may be made of materials that are pressure- and/or temperature-sensitive to adjust favorably to different environments to minimize changes in optical physics, or alternatively the changes in characteristics of the lens material (volume, shape, reflective index, transparency, etc.) result in deviations of the collected light properties, which can be used and correlated to aid in pressure/temperature measurements.

In one or more embodiments, the light source 101 is a lamp, light-emitting diode (LED), organic light-emitting diode, polymer light-emitting diode, active-matrix organic light emitting diode (AMOLED), any type of laser including but not limiting to laser diodes, as well as light emitting electrochemical cells, electroluminescent wires or any other component capable of emitting light. In such embodiments, the light source may be operable to emit light at substantially one wavelength or in certain narrow wavelength ranges (aka windows or bands) around a wavelength peak. Examples of such ranges of wavelengths around certain wavelength peaks are +/−1 nm, +/−2 nm, +/−5 nm, +/−10 nm, and +/−20 nm, and so on (e.g., 620 nm+/−20 nm). The light source 101 may emit light in the visible spectrum, infrared (IR) spectrum, ultraviolet (UV) spectrum, or a combination thereof. The light source 101 may emit coherent (e.g., monochromatic or laser) and/or polarized light.

In one or more embodiments, the cap 104 may provide a seal either for the device 100 (e.g., for the light-carrying body 102) or the medical tool (e.g., for the needle initially, for a scalpel as discussed herein, etc.). For example, the cap 104 may complete a partial or hermetic seal of the inner portion of the light-carrying body 102. Accordingly, the cap 104 may block the entrance of debris, fluid, blood, and particles during the performance of procedures.

In one or more embodiments, the cap 104 may be substantially spherical (as depicted in FIG. 1B), cubical, cubical with rounded corners/edges, conical, or a polyhedron. In one or more embodiments, cap 104 may match the external profile of the medical tool to provide a substantially continuous and flush surface (e.g., flush with the plane defined by the needle bevel 111 or continuous with the blade of a scalpel as discussed herein). Further, the cap 104 may be transparent or at least semi-transparent (e.g., 1-100% transparent as opposed to 0% or completely opaque) to allow the passage of light (or include light-filtering material operable to filter particular wavelengths).

In one or more embodiments, the cap 104 and/or the lens 103 include or are made from materials operable to act as parts of hydration sensor(s) (e.g., water absorbing components like hydrophilic polymers). Changes in tissue hydration can result in geometrical changes in the cap 104 and/or the lens 103, which in turn can result in changes to the proximate optics (e.g., lens focal point, reflectance, intensity of collected light, etc.). For example, in one embodiment one or more light detectors may be optically coupled with a hydration-sensitive lens and a hydration-insensitive lens. Changes in the measured light characteristics between the two lenses can indicate how the hydration-sensitive lens changed in shape. The change, matched with predetermined lens-behavior calibrations can indicate levels of hydration, temperature, and/or pressure. In some other example, lenses can be aligned in the longitudinal direction of the light-carrying body, with the front surface of the lens (e.g., facing the tissue), made from hydration-sensitive materials, in this example the changes in properties in the front lens results in deviations in the light which can be more enhanced for detection as the deviated light beams travel through the second lens and back to the light-carrying body. Accordingly, in some embodiments, measurements of hydration may be used to adjust the analysis to take into account the changes to the optics or further increase the accuracy of tissue detection.

In some embodiments, in addition to utilizing the changes in characteristics of cap 104 and/or lens 103 as a method to analyze and measure tissue hydration, the device 100 utilizes light sources 101 and/or light detector(s) 105 in certain windows of excitation and/or sensitivity wavelengths to measure hydration. In such embodiments, applying two different techniques to measure hydration ((i) change in absorbance of light from tissue and (ii) changes in the dimensions of the lens/cap and therefore collected reflectance) may increase the device 100 sensitivity and fidelity.

In one or more embodiments, the cap 104 and/or the lens 103 may be coated with layer(s) of polymers that contain sensitive dyes (also known as analyte-sensitive dyes), that can be excited at certain wavelengths and their emission provides information regarding concentrations of analytes including but not limited to oxygenation, SpO2, local pH, CO2 level, ions levels and so on. Examples of such dyes include but are not limited to PBFI, SBFI, Alexa Fluor™, Magnesium Green, and Oregon Green™. In some embodiments, the dye is Pt(ll) meso tetraphenyl tetrabenzoporphoryn (PtTPTBP), PtOEP, PdOEP, PdTBP(CO2Bu)8, PtNTBP, PdNTBP, Oxyphor R2, Oxyphor G2, PtTCPP, Ir(lll), Pt(ll), Ir(ppy)3, and the like. In some embodiments, the cap 104 and/or the lens 103 are coated with a dye operable to limit and filter the light emitted toward the tissue and reflected back from the tissue to the device 100.

In one or more embodiments, the cap 104 and the lens 103 may be the same component. For example, FIG. 1A shows the lens 103 also acting as the cap 104 or vice versa.

In one or more embodiments, the light detector 105 may be coupled with the base 109 and/or located such that it is operable to receive light that travels along the light-carrying body 102 (guided either by the light-carrying body 102 itself or optical fiber(s) within the light-carrying body 102). In one or more embodiments, the light detector 105 may be coupled with an optical fiber. In some embodiments, the light detector 105 is operable to measure the characteristics of light (e.g., wavelength, intensity, phase, direction, coherence, polarity, combinations thereof, etc.). The light detector 105 may be a photo transistor, photodiode, charge-coupled device (CCD), quantum device optical detector, photogate, or photoconductor, or any other component capable of detecting light. In some embodiments, the light detectors may be of the type used in complementary metal-oxide-semiconductor (CMOS) active-pixel sensors (APS). In some embodiments, the light detectors may be photodiodes. Representative examples of suitable photodiodes include, but are not limited to, P-N photodiodes, PIN photodiodes, and avalanche photodiodes. In some embodiments, P-N photodiodes and other types of photodiodes used in CMOS APS are used.

In some embodiments, the light detector(s) are coated or adhered to optical filtering layers to limit the wavelength of their detection to a certain window. In such cases, the filtering layers can be chosen to pass wavelengths higher or lower than a threshold. In similar cases, one or more optical filter layers can limit the passing wavelength to be lower and higher than an upper and lower threshold, respectively. In yet another embodiment, the light detector is inherently sensitive to a certain window of wavelengths.

In one or more embodiments, the controller module 106 (also referred to as data acquisition/processing module herein) is communicatively coupled with the light source 101 and light detector 105. As depicted in FIG. 1A, the controller module 106 may be local/connected to the device 100, but in other embodiments, the controller module 106 may be partially or completely external to the device 100.

In some embodiments, the controller module 106 controls the light source 101. For example, the controller module 106 may activate/deactivate the light source 101, cause the light source 101 to emit light at particular wavelengths, intensities, phase, etc. In some embodiments, light source may be operable to emit light at substantially one wavelength or in certain narrow wavelength ranges around a wavelength peak. Examples of such ranges of wavelengths around certain wavelength peaks are +/−1 nm, +/−2 nm, +/−5 nm, +/−10 nm, and +/−20 nm, and so on (e.g., 620 nm+/−20 nm). For example, an LED may include a narrow band of emission with a peak of 620 nm and narrow band of +/−5 nm around that peak. In some embodiments, the controller module 106 controls the light detector 105. For example, the controller module 106 may activate/deactivate light detector 105, cause the light detector 105 to measure light characteristics, etc. Further, the controller module 106 may receive light measurement information from the light detector 105.

In one or more embodiments, the controller module 106 analyzes the light characteristics information (i.e., provided by the light detector 105), thereby analyzing the tissue (or any other type of media). For example, the controller module 106 may cause the light source 101 to emit light with particular characteristics, the emitted light travels along the light-carrying body 102, and out through the lens 103. When the emitted light encounters tissue, at least some light will reflect back toward the lens 103. Accordingly, the reflected light (called reflectance) will travel back in through the lens 103, along the light-carrying body 102, and toward the light detector 105. Ultimately, at least some of the reflectance will reach the light detector 105. The controller module 106 may analyze the characteristics of reflectance, with respect to the particular characteristics of the emitted light, to determine characteristics of the tissue.

In some examples, a ratiometric analysis of light absorbance by tissue and therefore collected intensity at different wavelengths can provide information about the surrounding tissue, upcoming tissue in the trajectory of the insertion, as well as information regarding the tissue's characteristics including its oxygenation, hydration, and the like. In another example, when the light source 101 emits infrared light, analysis of the reflectance can provide information about the temperature of the tissue and/or material.

In yet another example, in which the lens or cap are coated with light-sensitive dye materials, light emission decay analysis may be performed to determine characteristics of the tissue and its analyte levels. For example, the light source 101 may flash/pulse (or otherwise change from an activated to deactivated state, or vice versa), while the light detector 105 measures the decay (activated to deactivated state) of the emitted light over time. Based on the decay properties, determinations may be made about the tissue.

In still another example, the device 100 can include multiple light sources 101 that can excite tissue at different wavelengths and multiple light detectors 105 that can measure the reflectance in individual windows of wavelengths. In such embodiments, a spectral analysis of absorbance at different wavelength windows can provide additional information regarding characteristics of the surrounding medium, such information can include but are not limited to oxygenation, hydration, SpO2, pH, as well as levels of analytes and biomarkers.

In one or more embodiments, the device 100 may adjust or calibrate to an environment to reduce noise/interference and thereby increase the accuracy of the analysis. For example, while the light source 101 is not emitting light, the light detector 105 may measure the existing ambient light (e.g., at or near the radiating and collecting portions of the device 100, also referred to as the probe portion/end herein). The analysis may then take into account the existing ambient light when the reflectance caused by light source 101 emission is analyzed (e.g., adjust the measured reflectance values to generate an effective reflectance value to be used in the analysis).

In one or more embodiments, the device 100 may determine confidence levels with respect to the analysis. For example, the controller module 106 may determine a confidence level associated with a determination that a tissue in a particular direction and distance is of a certain type. The confidence level may be communicated to a user in order to help the user assess how much the analysis can be relied upon.

It should be appreciated that the device 100 may analyze the immediate as well as upcoming tissue(s) along the trajectory of insertion even before an insertion is commenced, by analyzing the light that penetrates and is reflected upon the tissue and deeper tissue(s) that the device 100 (and thereby the lens 103 and/or cap 304) is in contact with. In other words, the outer skin layer or epidermis. As the insertion begins and continues, the device 100 may continue to analyze and report the type of the surrounding tissue as well as the type of the upcoming tissue in the trajectory of the insertion, for example, muscle, fat, vein, artery, nerve tissue, skeletal, and the like.

It should be appreciated that, in some embodiments, the controller module 106 may provide the "raw data" (i.e., light source 101 emitted light characteristics and light detector 105 measured reflectance characteristics) to a remote module that performs the analysis. In some embodiments, the remote module is an external device (e.g., which can include computers, laptops, tablets, smart phones, smart TVs, wearable devices, cloud software platforms).

In one or more embodiments, indicator 107 is coupled with the base 109 and/or located such that it can be viewed/heard/felt by a user or otherwise communicate information to the user. In some embodiments, the indicator 107 includes a display (e.g., an LCD screen or multiple LEDs), an audio source (e.g., audio speakers), and/or a haptic feedback component.

In some embodiments, the indicator 107 is communicatively coupled with the controller module 106 or the remote module. The controller module 106 or the remote module may cause the indicator 107 to communicate information related to the analysis to a user (also referred to as feedback herein). Specifically, the controller module 106 or the remote module may cause the indicator 107 to communicate information about the analyzed tissue to a user.

For example, an LCD-based display may include images, values, statements of advice, etc. In another example, one or more LEDs may provide feedback indicated by different colors, color combinations, intensities, blinking, etc. In yet another example, speakers may provide feedback in the form of beeping sounds, statements of advice, etc. In a further example, a haptic feedback component may provide feedback in the form of physical vibrations, forces, motions, etc.

In some embodiments, the communicated information about the analyzed tissue (or feedback) may be indications of the type/absence of tissue immediately surrounding a portion of a medical tool (e.g., muscle, fat, skeletal, epithelial, smooth, nerve, air cavity, blood vessels, etc.), the type of tissue farther away from the medical tool than the immediately surrounding tissue based on the current reflectance, the type of tissue farther away from the medical tool than the immediately surrounding tissue based on the tissue recently traveled through by the medical tool and/or the characteristics of reflectance from the emitted light, which is intentionally in ranges of wavelengths that can penetrate deeper into the tissue (e.g., near infrared range of the spectrum), and/or the type of superficial tissue (top/outside layer(s)) near a potential target insertion/procedure area. For example, in cases in which the target tissue is an airway, the device can predict and report proximity and arrival at the airway based on changes in the intensity of the reflectance prior (using light that can travel deeper into the tissue) and after arrival to the airway.

In some embodiments, the communicated information about the analyzed tissue may be indications of the changes in tissue characteristics (e.g., changes in density, temperature, pressure, oxygenation, SpO2, etc.) as the device 100 is moved. For example, changes in tissue density (as opposed to or only tissue type identification). In another example, when the collected light and thus media characteristics match that of an infection site. Which may be useful, for example, when searching for an infection site inside an internal organ, such as that caused by a bullet wound. Accordingly, a user may be notified when the device 100 has reached the targeted region, allowing the user to more accurately perform medical procedures (e.g., inject medicine(s) like drugs/antibiotics, collect samples, administer UV/IR light treatment, and so on).

For example, based on the analysis of the environmental media proximate to the radiating and collecting portions of the device 100, the device 100 may communicate that an injury or infection site has been reached. In one example, the light source 101 may emit UV light (i.e., UV-A, UV-B, or UV-C) radiation to sterilize an infection site. In another example, the light source 101 may emit IR light (i.e., near IR-A, near IR-B, near IR-C, or far IR) radiation to rehabilitate an injury area (e.g., by use of therapeutic windows in the mid-600 nm and mid-800 nm wavelengths).

In some embodiments, the feedback is in the form of text (e.g., displaying the name of the tissue type), percentages (e.g., of feedback accuracy certainty), directions (e.g., of target tissue types/areas), distances (e.g., of target tissue types/areas), and/or verbal statements of medical tool guidance advice (e.g., toward target tissue types/areas).

In one or more embodiments, the indicator 107 includes an interactive user interface operable to receive user inputs (or the controller module 106 is operable to receive user inputs from an external device). A user may be able to input information related to the procedure to aid the controller module 106 in the analysis and/or feedback. For example, the user may indicate a target region and/or entry point. With such information, the controller module 106 analysis can be supplemented when making determinations about the current or proximate tissue type (e.g., based on what tissue types have been encountered along the way, what tissue types are expected to be encountered, etc.). Additionally, in some cases, certain wavelengths of emission can be utilized to provide photonic reflectance feedback from the tissue deeper inside with respect to the insertion (or probe) tip. Using such information matched with input information about the type of insertion and targeted area, the indicator 107 can then communicate what tissue types are expected to be encountered next and/or when the target region has been reached.

In some embodiments, the targeted tissue is selected before the insertion/procedure by the user, based on the type of the targeted tissue, the device 100 may utilize only certain light sources 101 and/or light detectors 105. In some embodiments, based on the type of the targeted tissue, the device 100 may analyze the data differently (e.g., the controller module may apply a specific algorithm corresponding to the targeted tissue type). In addition, depending on the type of the insertion, the type of targeted tissue and the user (for example medical practitioner vs soldier in a battle field), the device may show selective information to guide the insertion/procedure.

Figure 10B:
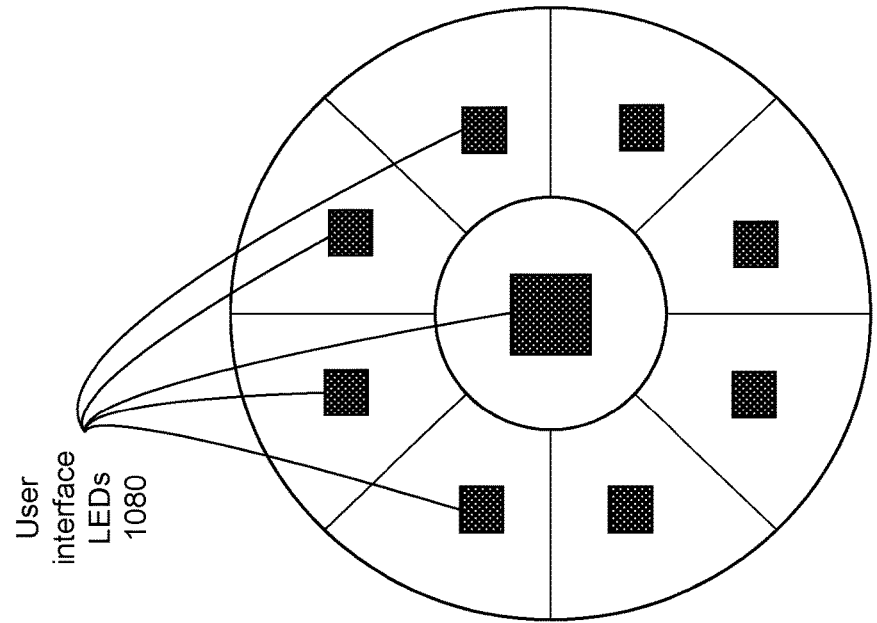
FIGS. 10A and 10B show indicator displays of a light-based medical device, in accordance with one or more embodiments.
Figure 10A:
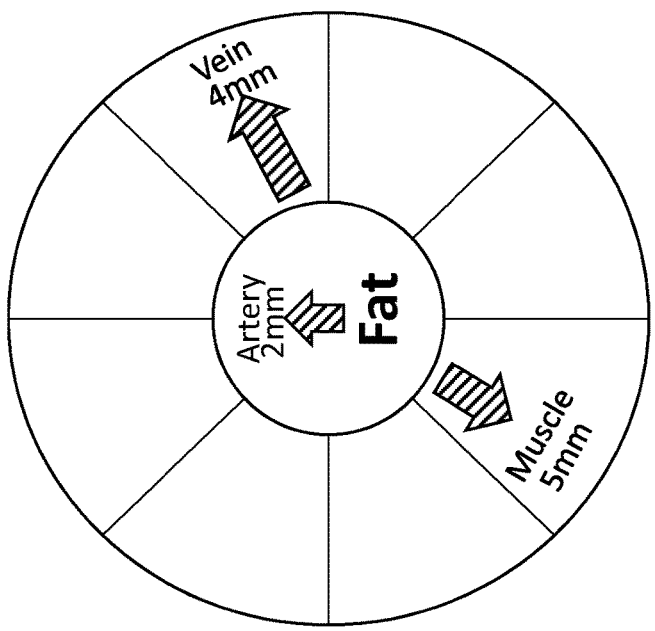

For example, turning to FIG. 10A, which shows an example of an indicator display 1007, the indicator display 1007 may provide feedback related to the tissues in various directions based on the tissue analysis. For example, the indicator display 1007 may indicate that fat tissue currently exists at or near the current location of the device 100, muscle tissue exists for the next or in 5 millimeters in a particular direction with respect to the device 100 (e.g., at ~245° in the xy-plane), a vein exists for the next or in 4 millimeters in a particular direction with respect to the device 100 (e.g., at ~25° in the xy-plane), and an artery exists for the next or in 2 millimeters in a longitudinal/axial direction with respect to the device 100 (e.g., along a z-axis "into the page" or into the body).

In another example, the indicator display 1007 guides a user toward a target area/tissue type specified by the user. In yet another example, the indicator display 1007 warns and/or guides a user away from particular area/tissue types (e.g., non-targeted organs, veins, arteries, nerves, membranes, etc). Thereby, unnecessary tissue damage can be avoided.

In some embodiments, the indicator display 1007 may provide 3-dimensional direction indications. For example, the display elements of the indicator display 1007 may indicate a 3D vector in the xyz-space in the direction and distance for a particular tissue.

It should be appreciated that the indicator display 1007 depicted in FIG. 10A is only one non-limiting example of an indicator 107. For example, the indicator display 1007 depicted in FIG. 10B includes user interface LEDs 1080 that may illuminate to provide feedback. In one example, the user interface LEDs 1080 may illuminate one at a time, or in combination, to indicate which type of tissue (e.g., communicated by particular LED colors), is in which direction (e.g., communicated by which LEDs illuminate), at what distance (e.g., communicated by particular LED intensities), and with what confidence level (communicated by particular LED pulse frequencies). In another example, the indicator display 1007 may include an LCD or OLED display. Displays like those discussed with respect to FIGS. 10A and 10B may be used for targeted insertion procedures which involve medical tool insertion into a certain tissue/location. For example, into the jugular vein or into the airway in the case of a cricothyrotomy or hemothorax.

Returning to FIG. 1B, in one or more embodiments, the communication module 108 is operable to communicate (send and/or receive) information in real time. For example, the communication module 108 may be communicatively coupled with the controller module 106, and thereby operable to communicate information from and/or to the controller module 106. For example, the communication module 108 may communicate through a wired or wireless communication medium. In another example, the communication module 108 may communicate with computers, laptops, tablets, smart phones, smart TVs, wearable devices, cloud software platforms, and so on.

In some embodiments, via the communication module 108, the controller module 106 may communicate data related to or including the analysis. For example, the "raw data" (i.e., light source 101 emitted light characteristics and light detector 105 measured reflectance characteristics) to a remote module that performs the analysis. The communication module 108 may then receive information resulting from the remote analysis (e.g., about the tissue) from the remote module. The controller module 106 may communicate the remote analysis information to the indicator 107 (e.g., for feedback to a user), communicate the analysis information to any other module operable to provide feedback, use the analysis information to further an analysis operation, and/or use the analysis information to modify control of the light source 101 or light detector 105.

It should be appreciated that while feedback communication has been discussed with respect to the indicator 107 of FIG. 1A and the indicator display 1007 of FIG. 10A, the indicator can be remote from the device. For example, the indicator display 1007 may not be directly attached to the device 100 (e.g., instead communicatively coupled through a wired or wireless communication medium via the communication module 108). In another example, the remote module or external device may be the indicator. For example, a tablet device screen, speaker, and/or haptic feedback elements (e.g., controlled by a "smart app" executed by the table device).

In some embodiments, the controller module 106 may be partially or completely controlled by the remote module (e.g., via the communication module 108). For example, a tablet device connected wirelessly through the communication module 108 to the controller module 106.

It should be understood that while a medical implement/tool is discussed with reference to the needle 110 in FIGS. 1A-1D, a needle is simply discussed for illustrative purposes and the device 100 may be used with various other types of medical implements/tools. For example, various other types of medical implements/tools like trocars or other sharps including but not limited to tweezers, scissors etc. Further, it should be understood that various aspects, concepts, and features discussed with reference to FIGS. 1A-1D (or any other figures for that matter) may be applicable to the embodiments discussed with reference to the other figures.

Figure 7B:
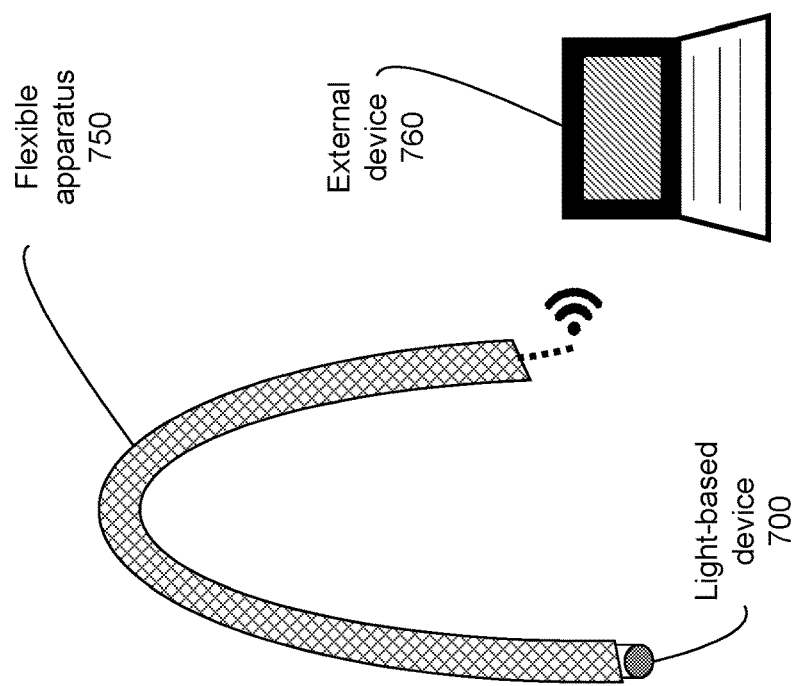
FIGS. 7A and 7B show a light-based medical device and a flexible apparatus, in accordance with one or more embodiments.
Figure 7A:
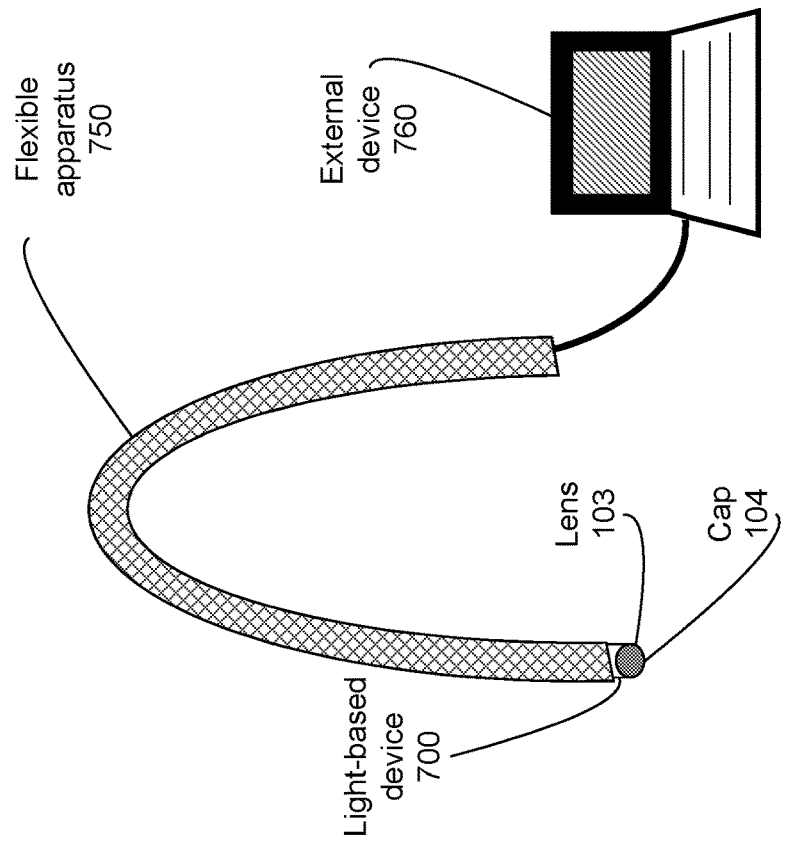

Further, it should be appreciated that the light radiating and collecting portions of the device 100 (e.g., the probing portion(s) including the lens, cap, and/or optical fiber ends discussed herein) may be positioned in different areas of a medical device, depicted in FIGS. 7A-7B as non-limiting examples. For example, in the case of a trocar, in the blade, the suction tube, or the cannula.

In some embodiments, the device 100 (and/or the light radiating and collecting portions) may be positioned in the guided wire used in TIPS procedure (Transjugular Intrahepatic Portosystemic Shunt). In this or similar procedures, the device 700 may help guide a user with an incision/insertion in the jugular vein and/or detect when the tip reaches the targeted hepatic vein. In some embodiments, the device 700 may be positioned in a needle for penetrating through the liver from the hepatic vein to reach the major branch of the portal vein, and thereby guide and detect the proper placement.

FIG. 2A shows the light-based medical device 100 with an optical fiber, in accordance with one or more embodiments. In one or more embodiments, the device 100 includes an optical fiber 221 coupled with the light source 101 and/or the lens 103. The optical fiber 221 may extend from the base end of the device 100 (e.g., the portion of the device including the light source 101), along the light-carrying body 102, and to the insertion end of the device 100 (e.g., the portion of the device including the lens 103). In some embodiments, the optical fiber 221 extends from the light source 101 to the lens 103.

Accordingly, light emitted by the light source 101 may travel through the optical fiber 221 to the lens 103. As a result, the emitted light may be affected by less transmission loss/attenuation or interference. In the example of FIG. 2A, reflectance traveling in from the lens 103 may travel along the light-carrying body 102 and not through an optical fiber.

FIG. 2B shows the light-based medical device 100 with an optical fiber, in accordance with one or more embodiments. In one or more embodiments, the device 100 includes an optical fiber 225 coupled with the light detector 105 and/or the lens 103. The optical fiber 225 may extend from the base end of the device 100 (e.g., the portion of the device including the light detector 105), along the light-carrying body 102, and to the insertion end of the device 100 (e.g., the portion of the device including the lens 103). In some embodiments, the optical fiber 225 extends from the light detector 105 to the lens 103.

Accordingly, light received by the light detector 105 may travel through the optical fiber 225 from the lens 103. As a result, the reflected light may be affected by less transmission loss/attenuation or interference. In the example of FIG. 2B, the light emitted from the light source 101 may travel along the light-carrying body 102 and not through an optical fiber.

Figure 2C:
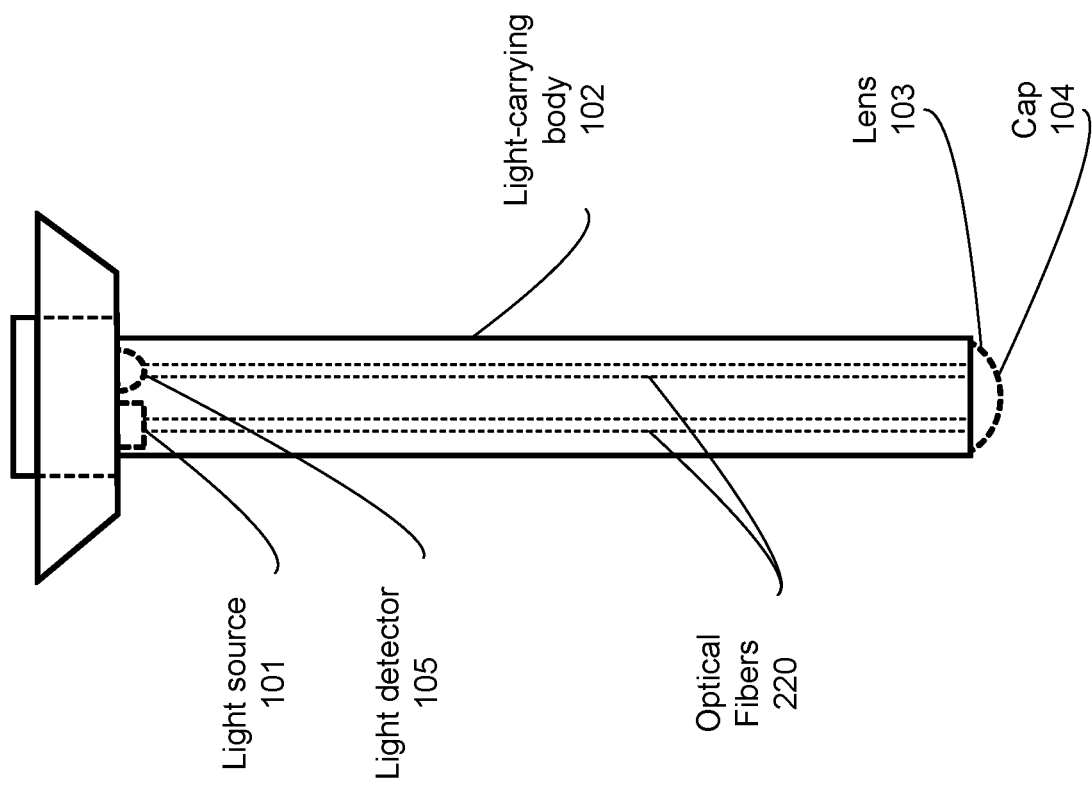

FIG. 2C shows the light-based medical device 100 with multiple optical fibers, in accordance with one or more embodiments. In one or more embodiments, the device 100 includes multiple optical fibers 220 (e.g., optical fibers 221 and 225) coupled with one or multiple light source(s) 101, and one or multiple light detector(s) 105, and/or lens 103. Optical fibers are described as transparent fibers that can transmit light. Examples of optical fibers include but are not limited to single mode fibers, multimode fibers, step-index fibers, graded index fibers, glass fibers and plastic optical fibers and combination thereof. Importantly, herein any component capable of transmitting and carrying light from the base end to the distal end of the device can be used instead of optical fibers in all embodiments. In this embodiment, some of the light detector(s) 105 may be coated with light-filtering layers for detecting the intensity of reflectance in certain windows of wavelengths. Accordingly, light emitted by the light source(s) 101 and/or received by the light detector(s) 105 may travel through the multiple optical fibers 220 (e.g., via optical fibers 221 and 225, respectively). As a result, both the emitted and reflected light may be affected by less transmission loss/attenuation or interference.

In one or more embodiments, the device 100 does not include a lens 103. Instead, the optical fibers 220 and/or light-carrying body 102 may carry the light to and from the cap 104. For example, the optical fibers 220 may extend from the light source 101 and/or light detector 105, to the cap 104, where light radiates from the end of the optical fiber coupled with the light source 101 (e.g., out of the cap 104 to the surrounding environment) and reflects back into the end of the optical fiber coupled with the light detector 105.

FIG. 2D shows the light-based medical device 100 with multiple optical fibers located inside the needle shaft 110, in accordance with one or more embodiments. Similar to FIG. 1D, the device 100 may be used in conjunction with a medical implement or tool. For example, FIG. 1D shows the device 100 located inside of the needle 110. Specifically, the light-carrying body 102 of the device 100 is located inside the needle shaft 110. However, the embodiment of the device 100 of FIG. 2D includes the multiple optical fibers 220. It should be appreciated that other embodiments are possible, for example, the device 100 may include only one optical fiber (e.g., optical fiber 221 or optical fiber 225), no optical fibers, or more/different optical fibers than optical fibers 221 and 225.

FIG. 3A shows a light-based medical device 300, in accordance with one or more embodiments. The embodiment of the device 300 depicted in FIG. 3A may be the same or similar to the embodiments of the device 100 discussed with reference to any of FIGS. 1A-1B and/or 2A-2C. In some embodiments, the device 300 depicted in FIG. 3A may include a base 109 with a narrower profile than the base depicted in FIG. 1A.

In one or more embodiments, the device 300 includes a cap 304 that is transparent (or include light-filtering material operable to filter particular wavelengths) and completes a partial or hermetic seal of the inner portion of the light-carrying body 102. The cap 304 may be the same or similar to the cap 104. In the example of FIG. 3A, the cap 304 is a discrete component different from the lens 103. In one or more embodiments, the cap 304 matches the external profile of a medical tool to provide a substantially continuous and flush external surface with the implement/tool. For example, in the case of a blade, the cap 304 may include a sharp cutting edge (e.g., made of a transparent ceramic or polymer).

FIG. 3B shows a medical implement or tool, in accordance with one or more embodiments. In the example of FIG. 3B, the medical implement/tool is a surgical blade 330 (e.g., scalpel). The surgical blade 330 includes a hollow channel 331, depicted by dotted/dashed lines, extending from a base end to an insertion/blade end. The hollow channel 331 may be shaped similarly to the device 300 and thereby able to accommodate the device 300. At the insertion/blade end of the surgical blade 330, the hollow channel 331 may result in an opening 332 of the surgical blade that matched the cap 304 of the device 300.

FIG. 3C shows the device 300 and the medical implement/tool, in accordance with one or more embodiments. The device 300 may be used in conjunction with a medical implement/tool. For example, FIG. 3C shows the device 300 located inside of the surgical blade 330. Specifically, the light-carrying body 102 of the device 300 is located inside the hollow channel 331.

In one or more embodiments, the cap 304 of the device 300 matches the external profile of the surgical blade 330 to provide a substantially continuous and flush surface (e.g., continuous with the sharp edge of the blade). Accordingly, any potential disruption to the function of the blade may be minimized or eliminated. Meanwhile, the device 300 may perform the tissue analysis in real time with the use of the surgical blade 330.

In one example, the device 300 may analyze the tissue even before an incision is commenced, by analyzing the reflection of the light from the tissue that the surgical blade 330 (and thereby the cap 304) is in contact with (in other words, the outer skin layer or epidermis). In addition, the device can analyze the reflectance from the tissue behind that contacted surface (skin layer or epidermis). In such embodiments, the correct location of the incision can be determined based on an analysis of the reflectance from the tissue the surgical blade is in contact with and/or the tissue that is farther inside, through utilizing light sources with wavelengths that can travel into the tissue (e.g., near infrared). In similar embodiments, the device can warn the user if the incision location (skin layer) is above or near a vein/artery or non-limiting examples of tissue(s) and/or organs to remain partially or fully undisturbed. As the incision begins and continues, the device 300 may continue analyzing the tissue.

FIG. 3D shows the device 300 with optical fibers and the medical implement/tool, in accordance with one or more embodiments. Similar to the embodiments of the device 100 depicted in FIG. 2C or 2D, the device 300 includes multiple optical fibers 220 coupled with the light source 101, light detector 105, and/or lens 103. It should be appreciated that other embodiments are possible, for example, the device 300 may include only one optical fiber, no optical fibers, or more/different optical fibers than the optical fibers 220.

Further, it should be understood that while a medical implement/tool is discussed with reference to a blade in FIGS. 3B-3D, a blade is simply discussed for illustrative purposes and the devices 100 and 300 may be used with various other types of medical implements/tools. For example, various other types of medical implements/tools like tweezers, scissors, and so on. Further, it should be understood that various aspects, concepts, and features discussed with reference to FIGS. 3B-3D (or any other figures for that matter) may be applicable to the embodiments discussed with reference to the other figures.

Figure 3G:
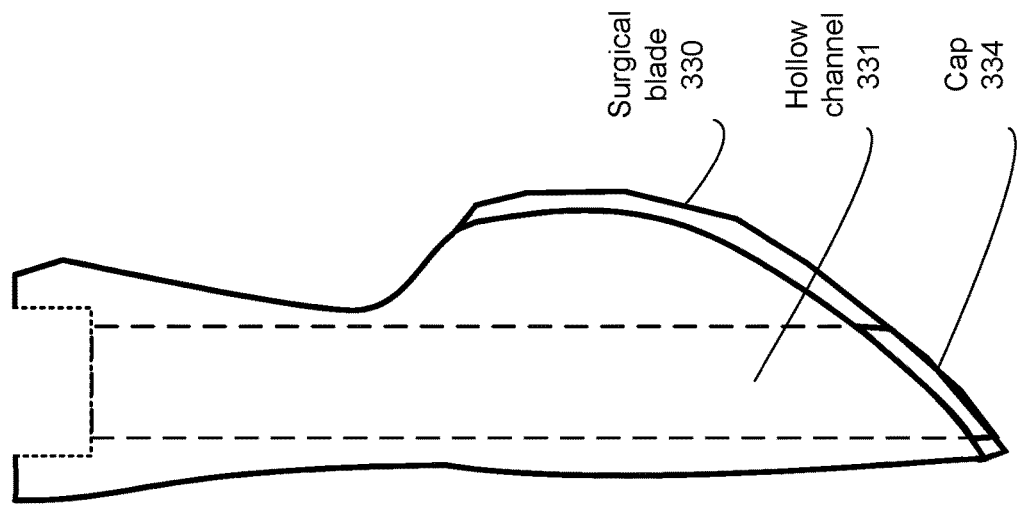

In one or more embodiments, the surgical blade 330 includes a cap. For example, FIG. 3G shows the surgical blade 330 with a cap 334. Like the surgical blade 330 discussed with reference to FIG. 3B, the surgical blade 330 of FIG. 3G includes a hollow channel 331 extending from a base end to an insertion/blade end. However, instead of having an opening 332 at the insertion/blade end, the surgical blade 330 includes the cap 334. The cap 334 may be transparent (or include light-filtering material operable to filter particular wavelengths) and provide a seal of the hollow channel 331.

Figure 3F:
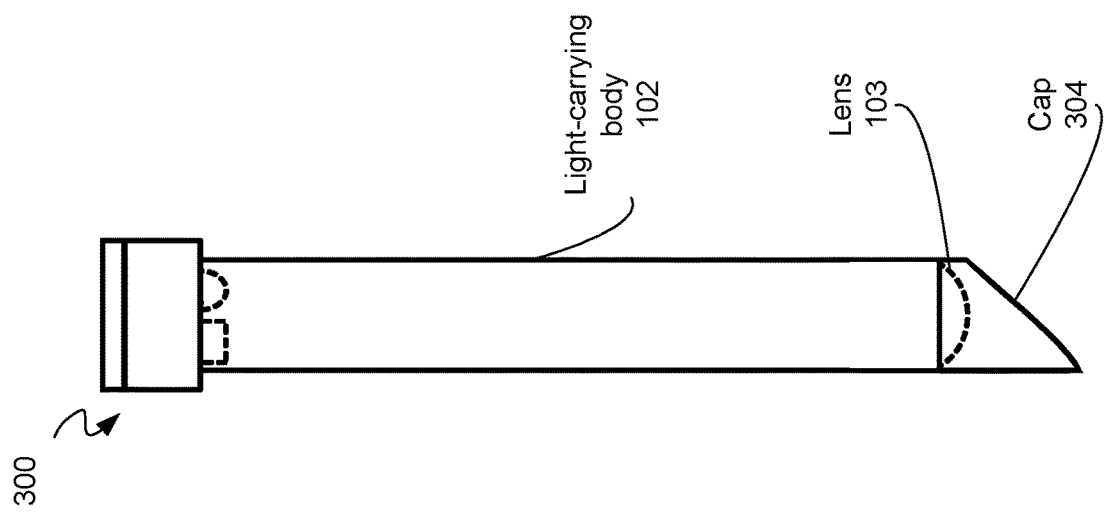
Figure 3E:
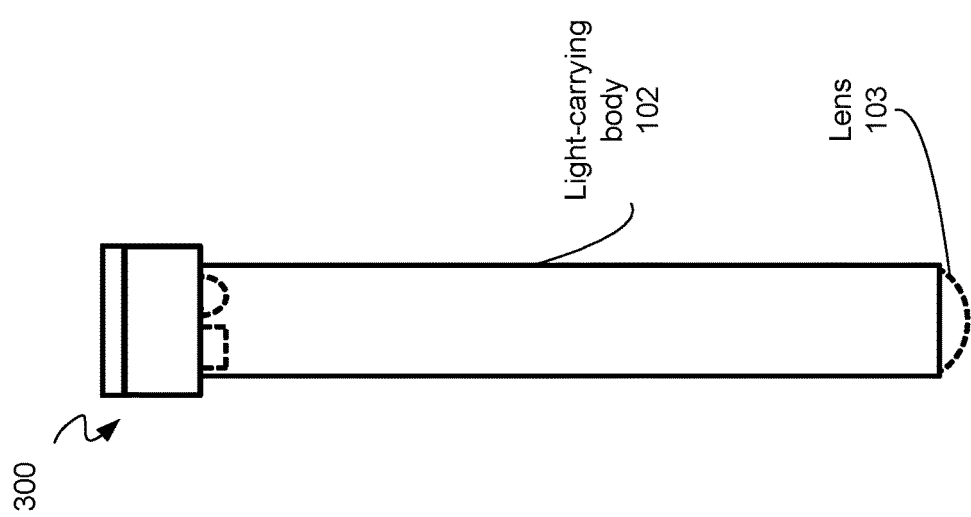

Meanwhile, FIGS. 3E and 3F show the device 300 with cap variations, in accordance with one or more embodiments. For example, FIG. 3E shows the device 300 without the cap 304 depicted in FIG. 3A (alternatively, the lens 103 acts as a cap). In another example, FIG. 3F shows the device 300 with a version of the cap 304 that extends less than the version of the cap 304 depicted in FIG. 3A. Because the version of the surgical blade 330 depicted in FIG. 3G already includes a cap 334, both embodiments of device 300 depicted by FIGS. 3E and 3F may be used with the surgical blade 330 depicted in FIG. 3G.

It should be appreciated that the cap 334, just like the cap 304 and therefore the cap 104, may have different geometries based on applications. The cap 334, just like the cap 304 and therefore the cap 104, may be made from one or more combination of different materials which can include at least one or more at least semi-transparent material with or without addition of non-transparent constituents.

Figure 4B:
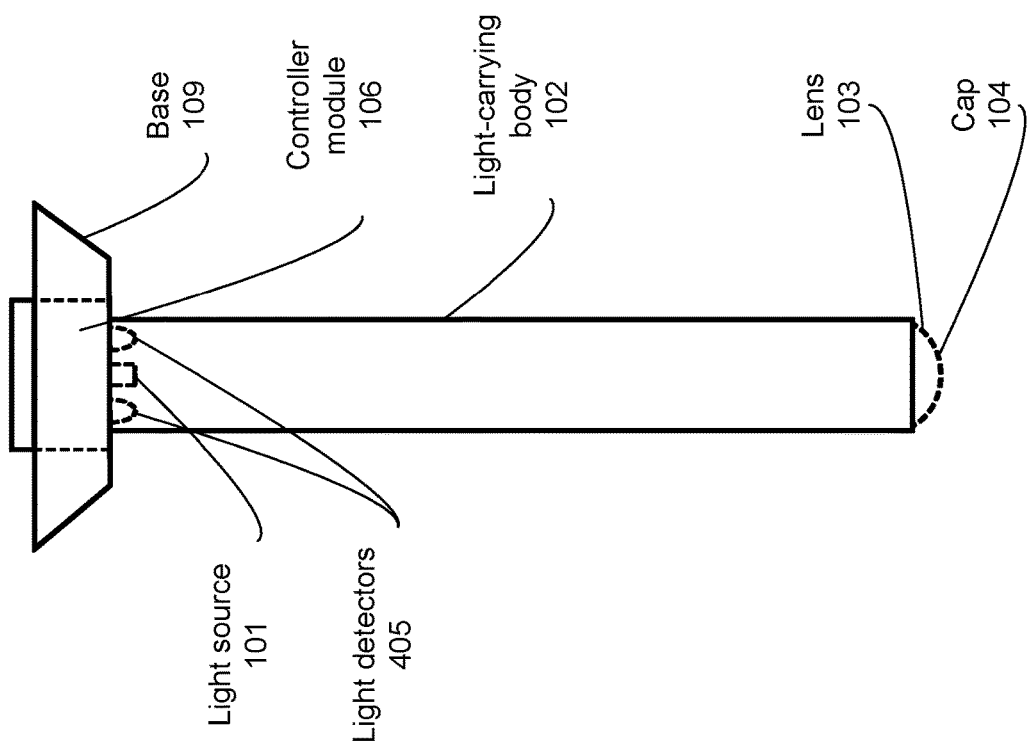
FIGS. 4A and 4B show a light-based medical device, in accordance with one or more embodiments.
Figure 4A:
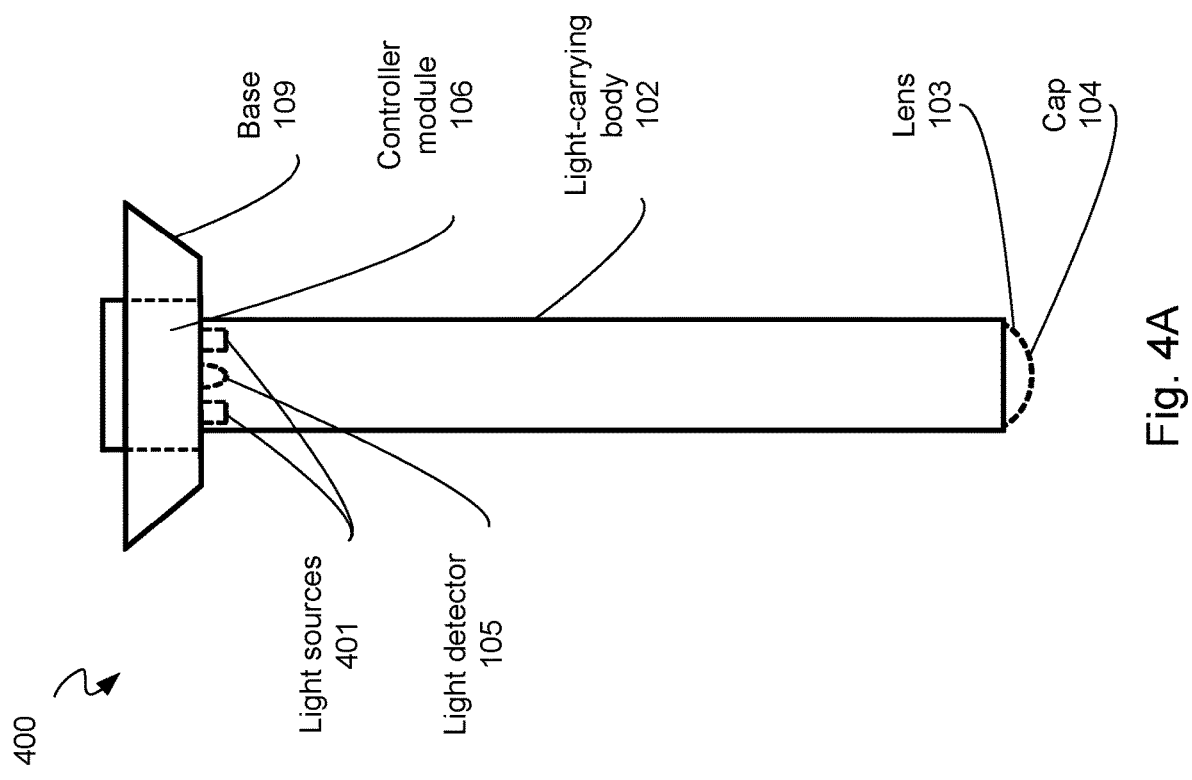

FIG. 4A shows a light-based medical device 400, in accordance with one or more embodiments. The embodiment of the device 400 depicted in FIG. 4A may be the same or similar to the embodiments of the devices discussed with reference to any of FIGS. 1A-1B, 2A-2C, 3A, and/or 3E-3F. However, the device 400 depicted in FIG. 4A demonstrates an embodiment of the device that includes multiple light sources 401. It should be understood that various aspects, concepts, and features discussed with reference to FIGS. 4A-4B (or any other figures for that matter) may be applicable to the embodiments discussed with reference to the other figures.

Multiple light sources may be used to provide various wavelengths, intensities, phases and/or directions of light. Further, each discrete light source of the multiple light sources 401 may emit light one at a time or in parallel with the other discrete light sources.

In the former case, the multiple light sources 401 may be activated according to a predetermined program (e.g., a clockwise illumination pattern) or according to tissue areas that require additional sampling. In the latter case, the multiple light sources 401 may provide further combinations of wavelengths, intensities, phases and/or directions of light. In either case, the light sources 401 may activate/deactivate rapidly (or pulse) such that many samples are taken per second (e.g., reflectance or pass-through light measurements), thereby providing real time and/or additionally precise/accurate raw data. Accordingly, the analysis of the tissue can be further aided by the additional wavelengths/intensities/phases/directions, or even further by the combinations of wavelengths/intensities/phases/direction.

FIG. 4B shows a light-based medical device 100, in accordance with one or more embodiments. The embodiment of the device 100 depicted in FIG. 4A may be the same or similar to the embodiment of the device 100 discussed with reference to any of FIGS. 1A, 1B, 2A, 2B, and/or 2C. However, the device 100 depicted in FIG. 4A demonstrates an embodiment of the device 100 that includes multiple light detectors 405.

Multiple light detectors may be used to measure various wavelengths, intensities, phases, and/or directions of light. Further, each discrete light detector of the multiple light detectors 405 may measure light one at a time (e.g., corresponding to activating/emission of one or more particular light sources) or in parallel with the other discrete light detectors. The multiple light detectors 405 may provide further combinations of wavelengths, intensities, phases and/or directions of light. Accordingly, the analysis of the tissue can be further aided by the additional wavelengths/intensities/phases/directions, or even further by the combinations of wavelengths/intensities/phases/direction.

In some embodiments, filtering or selectivity of particular wavelengths may be achieved by utilizing light detector(s) that are inherently sensitive to a certain range of wavelengths or application of light-filtering coating on top of the light detector(s) or by adhesion of a light filtering layer.

In some embodiments, the device 100 may include both multiple light sources 401 and multiple light detectors 405. In some embodiments, multiple light sources 401 and multiple light detectors 405 can yield additional information on the analyzed tissue, including but not limited to levels of hydration, SpO2, PO2, pH, CO2, as well as levels of analytes including but not limited to important biomarkers.

It should be appreciated that the device 100 may include multiple optical fibers 220 per light source 101, multiple light sources 401 per optical fiber (221 and/or 225), multiple optical fibers 220 per light detector 105, and/or multiple light detectors 405 per optical fiber (221 and/or 225).

Regardless of the combinations, in some embodiments, the emission direction/radius of the light source(s) and/or sensing direction/radius of the light detector(s) are angled with respect to the longitudinal axis of the light-carrying body 102. In some embodiments, the emission direction/radius of the light source(s) and/or sensing direction/radius of the light detector(s) are not all the same.

It should be appreciated that, none/some/all of the light sources and/or none/some/all of the light detectors discussed with reference to FIGS. 4A and 4B, may be coupled with optical fibers. For example, the embodiments depicted by FIGS. 4A and 4B do not show optical fibers. However, with reference to FIG. 4A, both the light sources 401 and light detector 105 may be coupled with optical fibers, the light sources 401 may be coupled with optical fibers while the light detector 105 is not, or the light detector 105 may be coupled with an optical fiber while the light sources 401 are not. Or with reference to FIG. 4B, both the light source 101 and light detectors 405 may be coupled with optical fibers, the light source 101 may be coupled with optical fibers while the light detectors 105 are not, or the light detectors 405 may be coupled with an optical fiber while the light source 401 is not.

FIGS. 5A-5D show an inside bottom view of the light-based medical device 100, in accordance with one or more embodiments. As discussed with reference to FIGS. 4A-4B, the device 100 may include multiple light sources 401 and/or multiple s 405.

Figure 5B:
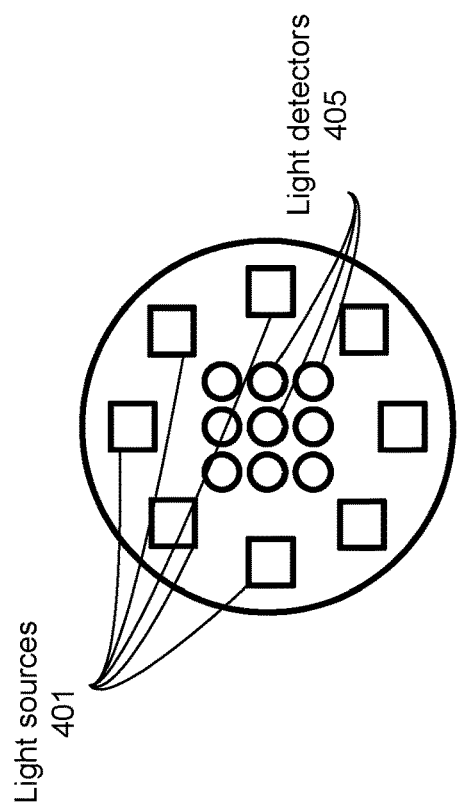
FIGS. 5A-5D show an inside bottom view of a light-based medical device, in accordance with one or more embodiments.
Figure 5D:
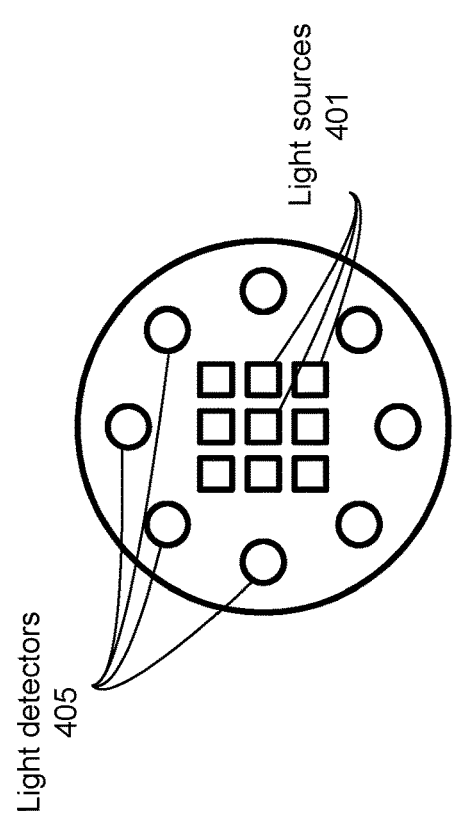
Figure 5A:
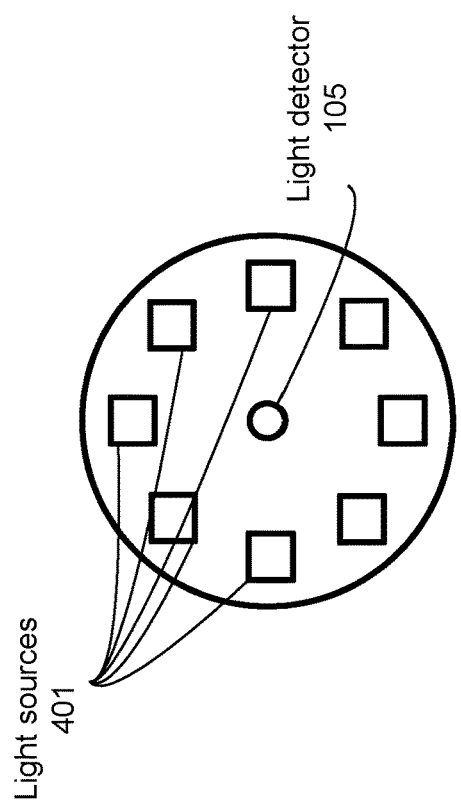
Figure 5C:
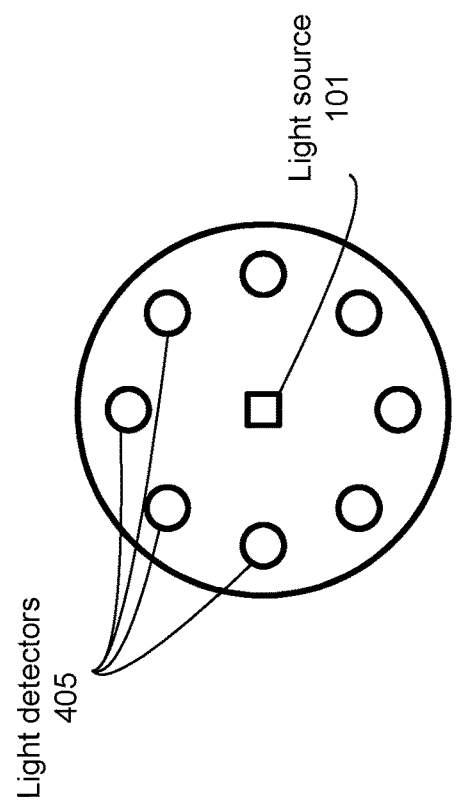

For example, as illustrated by FIG. 5A, the device 100 may include multiple light sources 401 distributed in an outer ring pattern and a light detector 105 at the center of the ring (e.g., coupled with the base 109). In another example, as illustrated by FIG. 5C, the device 100 may include a light source 101 at a center of an outer ring pattern and multiple light detectors 405 distributed as the outer ring pattern. In yet another example, as illustrated by FIG. 5B, the device 100 may include multiple light sources 401 distributed in an outer ring pattern and multiple light detectors 405 configured in a grid pattern at the center of the ring. In yet a further example, as illustrated by FIG. 5D, the device 100 may include multiple light sources 401 configured in a grid pattern at the center of a ring and multiple light detectors 405 distributed in an outer ring pattern.

It should be appreciated that any other light source and/or light detector configurations are possible. For example, multiple light sources 401 may be distributed in a ring pattern alternatingly with multiple light detectors 405.

FIGS. 6A-6G show a light-based medical device 600, in accordance with one or more embodiments. The embodiments of the device 600 depicted in FIGS. 6A-6G may be the same or similar to the embodiments of the devices discussed with reference to any of FIGS. 1A-1B, 2A-2C, 3A, 3E-3F, and/or 4A-4B. It should be understood that various aspects, concepts, and features discussed with reference to FIGS. 6A-6G (or any other figures for that matter) may be applicable to the embodiments discussed with reference to the other figures.

As shown in FIG. 6A, multiple optical fibers 220 may be coupled with the multiple light sources 401. The ends of the multiple optical fibers 220 may be located near/at different positions with respect to the lens 103. Accordingly, light emitted by each light source, and thereby its corresponding optical fiber, may encounter the lens 103 at different areas and/or different angles. As a result, the light will refract and radiate into different directions, as depicted by the refracted light 601.

Based on the reflectance resulting from the refracted light 601, an analysis with respect to the directionality of the tissue/medium can be performed. For example, the controller module 106 may cause each discrete light source of the multiple light sources 401 to emit light one by one, where the reflectance corresponding to each discrete light source is noted. Because the refraction/radiation direction corresponding to each light source is known, a directional analysis based on the reflectance (corresponding to each light source) can be performed.

For example, in an embodiment including four light sources positioned such that they form the four corners of a square (i.e., at 0°, 90°, 180°, and 270°, not shown) around a center-positioned light detector, the light emitted from the 0° light source, traveling through a corresponding optical fiber, and into the lens 103 at a nonzero distance from the center of the lens at 0°, can refract and thereby radiate an area of tissue that is substantially in the opposite direction of the area that the 180° light source will radiate.

It should be understood that various combinations of light sources (thereby also directions), intensities, and wavelengths may be used to provide further resolution to the analysis. It should also be understood that similar types of results may be achieved with various embodiments of the device 600. For example, with multiple light detectors 405. Or with fewer or no optical fibers, because light sources distributed along the base 109 may result in at least some variation in refraction at the lens 103. It should also be understood that, as discussed herein, various combinations of light sources and light detectors are possible. For example, the device 600 of FIG. 6A, in addition to having multiple light sources 401, could also include multiple light detectors 405 like shown in FIG. 6B (e.g., to increase the measurement resolution). It should also be noted, similar to what was previously described, that light detector(s) 405 can be chosen to have sensitivity at certain wavelengths windows, or can be coated with or be adhered to light-filtering layers.

In some embodiments, multiple optical fibers 220 may connect to the lens 103 orthogonally with respect the lens surface (the lens surface they intersect with) and at different lens locations. For example, the surface of the lens facing the optical fibers 220 (as opposed to facing the environment/analyte media), at the point or area of the lens the optical fiber contacts or extends closest to. For the sake of simplicity, consider the case of a spherical geometry in which different lines (optical fibers) connect to different locations at the surface of the sphere (lens) at different locations and that they are all pointing towards the center of the sphere. In such a case, the lines are all perpendicular to the sphere's surface. In these embodiments, the connecting ends of the optical fibers 220 to the lens 103 are angled with respect to the longitudinal axis of the light-carrying body 102. The light focused from the lens can radiate different locations within the tissue. It should be understood that these optical fibers can be connected to light sources 401 and/or light detectors 495 at the base 109.

As shown in FIG. 6B, in one or more embodiments, the multiple optical fibers 220 may be angled with respect to the lens 103. In other words, the multiple optical fibers 220 may include an angle other than 90° with respect to the lens 103 surface (in other words, not perpendicular or not orthogonal with the lens surface 103). In addition, the multiple optical fibers 220 may include an angle other than 0° with respect to the light-carrying body (in other words, not parallel with respect to the light-carrying body). For example, an angle of 1-89° or 91-179°. As a result, the refraction angle and area of the refracted light 601 may be increased.

In some embodiments, while the multiple optical fibers 220 are angled with respect to the lens 103, some or all of the multiple optical fibers 220 may reach the lens 103 at substantially the same point. However, their varying angles may still affect the refraction angle and area of the refracted light 601.

In some embodiments, an optical fiber may include two or more angles. For example, a portion nearer the light source may be at a 90° with respect to the lens 103 whereas a portion nearer the lens may be at a non-90° with respect to the lens. In another example, both portions may be at a non-90° with respect to the lens while at different angles with respect to one another (e.g., as depicted in FIG. 6B).

Figure 6D:
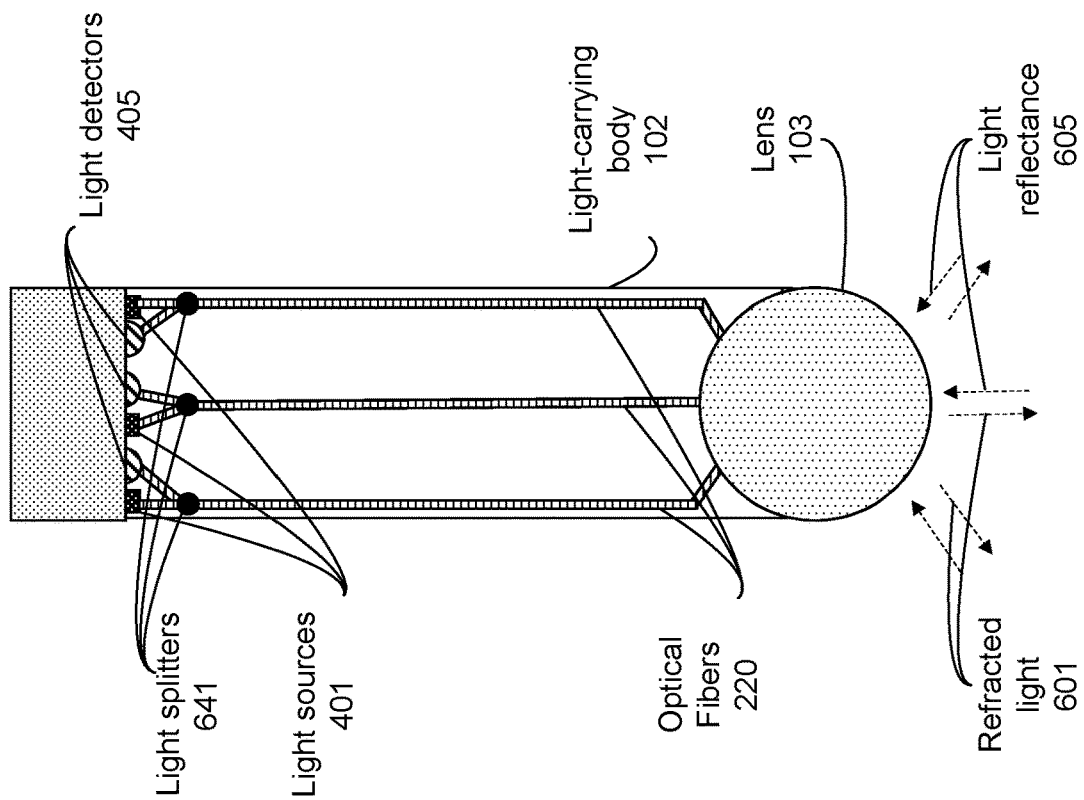
Figure 6C:
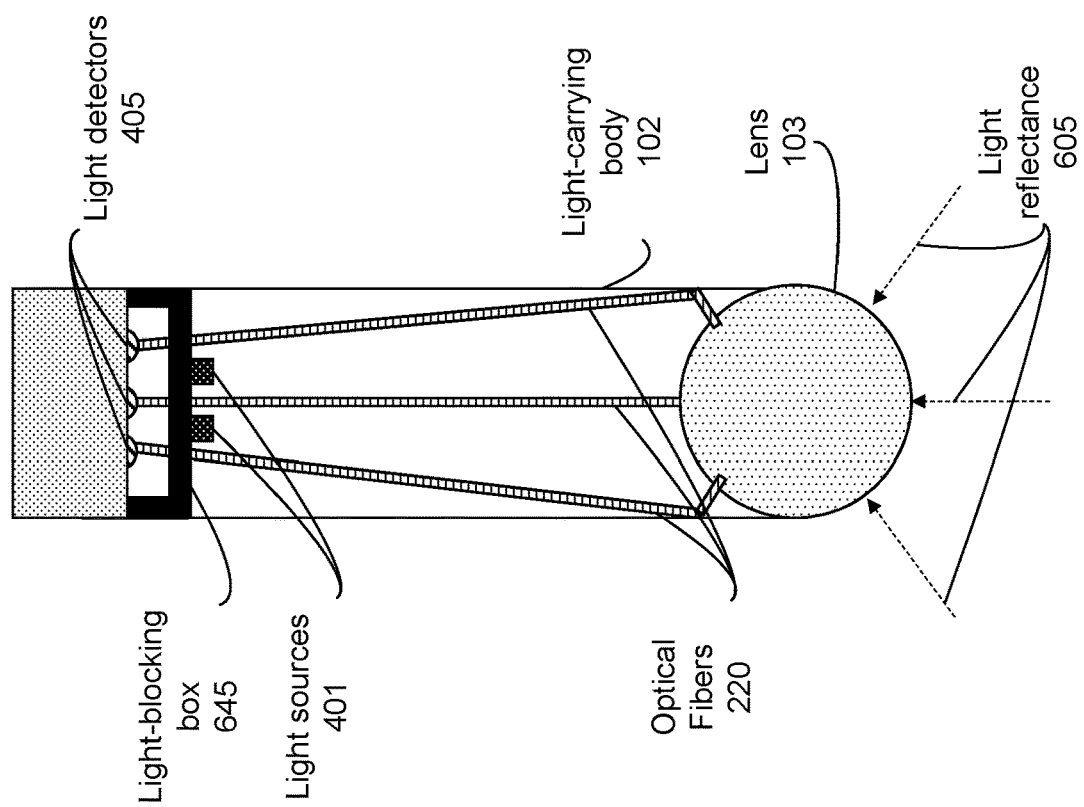

As shown in FIG. 6C, in one or more embodiments, a light-blocking box 645 may optically insulate one or more light detectors. For example, the light-blocking box 645 insulates the multiple light detectors 405, while optical fibers pass through the light-blocking box 645. Accordingly, the multiple light detectors 405 may be protected from interference. For example, from emitted light that travels to the light detector without having traveled out of the device, in other words, emitted light that may reflect/refract internally.

Figure 6F:
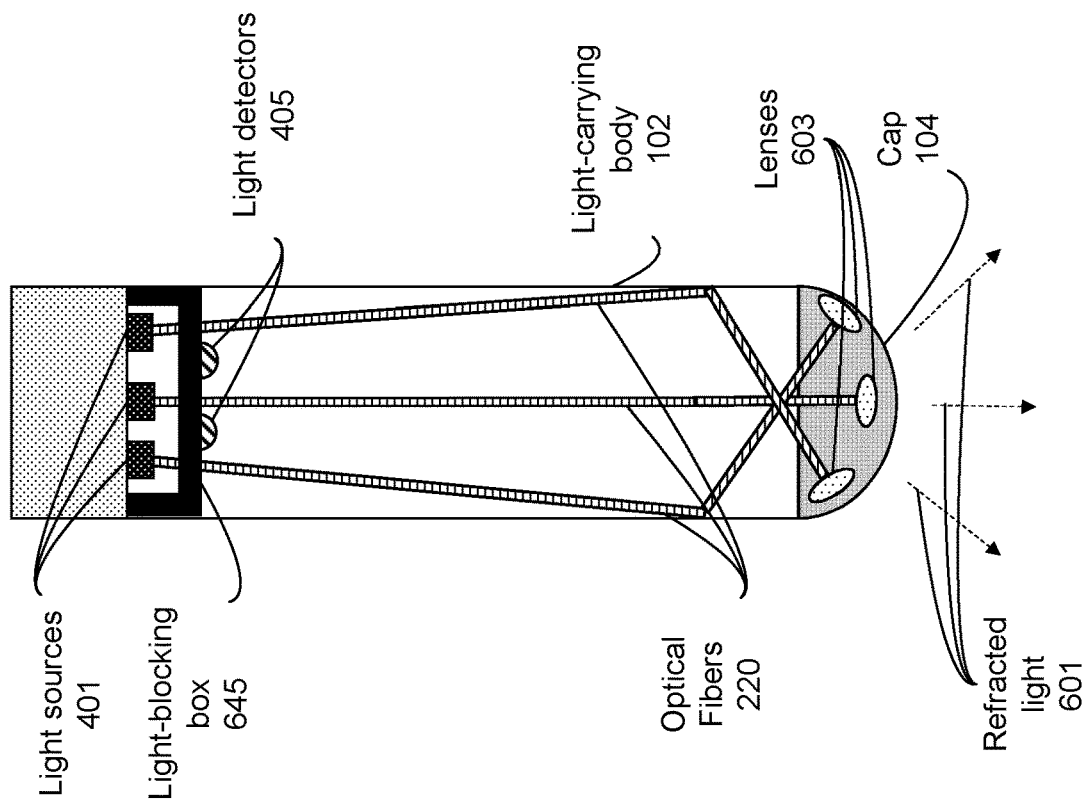

It should be appreciated that while FIG. 6C depicts the light-blocking box 645 with the light sources 401 at an outer side of the light-blocking box 645 and the light detectors 405 at an inner side of the light-blocking box 645, other configurations are possible. For example, both the light sources 401 and the light detectors 405 may be located at an inner side of the light-blocking box 645, or the light sources 401 may be located at an inner side of the light-blocking box 645 and the light detectors 405 at an outer side of the light-blocking box 645 as depicted by FIG. 6F.

It should be appreciated that while FIG. 6C depicts the light-blocking box 645 as being located proximate to the base end and with light sources 401 at an outer side of the light-blocking box 645, other configurations are possible. For example, the light-blocking box 645 may be located distal from the base end (e.g., more proximate to the insertion/probe end), with light sources 401 at an inner side of the light-blocking box 645 more proximate to the based end, and/or with light detectors 405 at an outer side of the light-blocking box 645.

Further, the multiple light detectors 405 may receive light only from particular areas of the lens 103. For example, the corresponding optical fibers, like those in FIGS. 6A and 6B with respect to the light sources, may each be positioned and/or angled differently with respect to the lens 103. As a result, each light detector may be guided light reflectance 605 from different areas. Therefore, the analysis may be further informed by the individual light reflectance characteristics at each light detector.

As shown in FIG. 6D, in one or more embodiments, light splitters 641 may group one or more light sources and/or one or more light detectors. A light splitter (also referred to as beam splitter herein) may split one or more optical fibers such that the optical fiber couples one or more light sources and/or one or more light detectors. Light splitters herein refer to any optical component capable of splitting the incident light at a designated ratio into two or more separate beams, such splitters can also be used in reverse to combine the two or different beams into one. Examples of such light splitters include but are not limited to polarized or non-polarized beam splitter cubes, highly reflection mirrors, fiber optic beam splitters, metal coated mirrors, pellicles, micro-optic beam splitters, waveguide beam splitters and combinations thereof. For example, as depicted in FIG. 6D, the light splitters 641 pair a light source and a light detector, such that the optical fibers coupled with either are combined at a junction where only one optical fiber continues toward the lens. Accordingly, such pairs (or larger groups) may work together to analyze different areas of tissue, while at the same time requiring less optical fiber.

It should be understood that light splitters can also be positioned at the lens end of the device to split the optical fiber to over two or more areas of the lens.

Figure 6E:
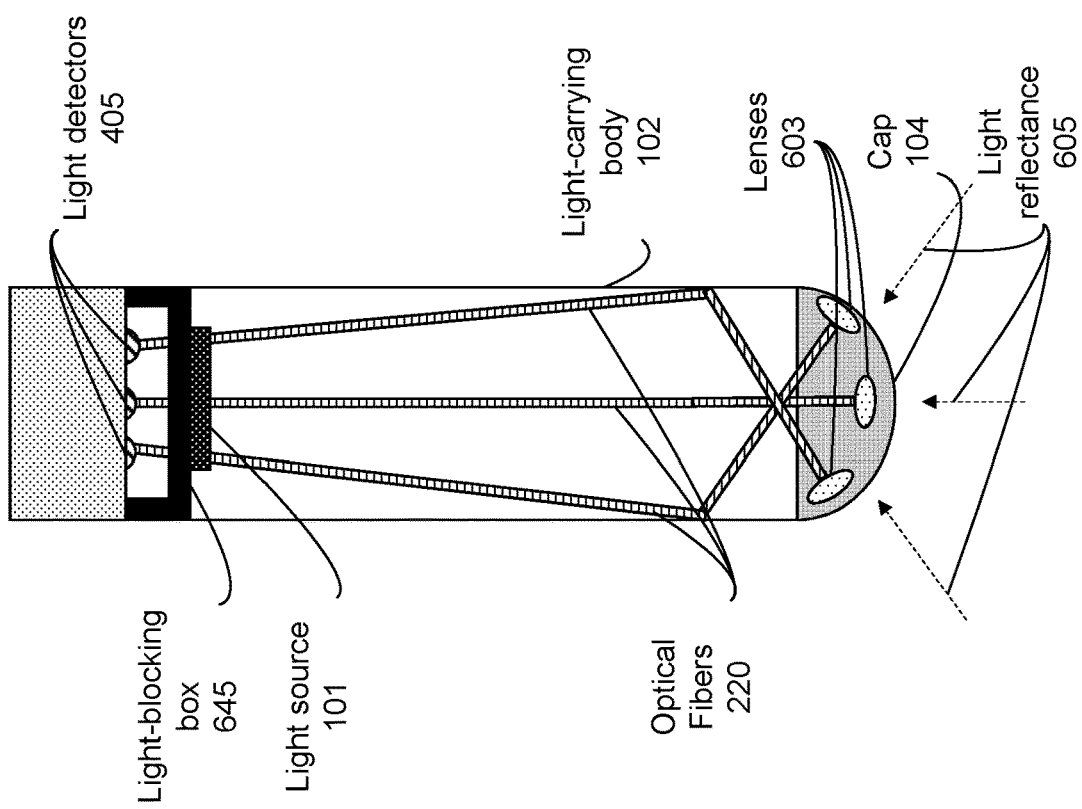

As shown in FIG. 6E, in one or more embodiments, multiple dedicated lenses 603 may be used with light detectors. For example, multiple lenses 603 may be included in a cap 104 (e.g., distributed side-by-side in a radial arrangement), may be part of a larger lens that includes various lens portions, may be positioned longitudinally (in other words some lenses 603 are in front/back of one another and light from one lens may travel through one or more lenses to reach the tissue and come back). Or the lenses 603 may be positioned in a way that multiple sampler lenses are behind one larger lens, or positioned otherwise. In some embodiments, the multiple lenses 603 may be coupled with optical fibers that are coupled with one or more light detectors (thereby dedicated) or one or more light sources. Accordingly, the excitation and reflectance received from each light source and by each light detector may be enhanced or affected by each corresponding lens.

In one or more embodiments, the multiple dedicated lenses 603 with corresponding light detectors may be used to measure local pressure and/or temperature.

In another example, lenses with different flexibility responses in response to changes in pressure/temperature may be included, where the measurement differences in reflectance or pass-through light between the different lenses may be used to perform an analysis resulting in pressure/temperature determinations. In such an example, the lenses may correspond to the light sources, light detectors, or both.

In one non-limiting examples (not shown), lenses are arranged longitudinally along the light-carrying body 102, the lens at the distal tip is made of minimally- or non-temperature/pressure sensitive material and the lens farther inside and more proximate to the base is made of temperature/pressure sensitive material. In this case, through using a temperature conductive light-carrying body, the temperature changes inside the light-carrying body 102 can then result in geometrical and/or optical characteristic changes of the lens inside (positioned closer to the base). In such a case, the changes to the reflected light can be determined and correlated back to the fluctuations of temperature in the surrounding environment.

In some embodiments, multiple lenses may be positioned longitudinally with respect to one another, where one or more of the lenses are pressure/temperature-sensitive. Because the shape of such lens(es) change as the pressure/temperature changes, in other words, one or more of the lens(es) change in geometry (e.g., convexity or concavity) their focal points and collected light intensity with respect to the perpendicular plane to the light-carrying body changes. Such changes in light can be analyzed to determine pressure/temperature characteristics.

In some embodiments, analysis of light intensity change because of the changes in lens geometries due to temperature/pressure fluctuations to measure temperature and/or pressure is matched with analysis of light as a technique to determine temperature change (e.g., use of infrared light to measure local temperature at the insertion tip). In such embodiments, light analysis of temperature can act as a reference for corrections to isolate the effects of pressure and temperature in changing the lens geometry and/or optical characteristics. Using both strategies described can result in a higher sensitivity and accuracy for measurement of both pressure and temperature.

In some embodiments (not shown), the light emitted may follow a closed-circuit path that never exits the cap nor the lenses. For example, a light source may be optically coupled through an optical fiber with pressure/temperature-sensitive lens(es), and light detector(s) are also optically coupled through optical fiber(s) with the pressure/temperature-sensitive lens(es), creating an internal loop or U-shaped path. Accordingly, the pressure/temperature measurement may include less interference/noise from the environment.

In some embodiments, the angle of the light and optical characteristics of the lenses (e.g., reflective index) are intentionally chosen such that the light is reflected back from both inside and outside surfaces of the lens. In other words, some of the light is reflected back from the outer surface of the lens that faces the light sources and is inside the light-carrying body. The remainder portion of the light enters the lens and reaches the inside surface of the lens closer to the insertion tip, based on angle, wavelength, and reflective characteristics of the lens material, the light is then reflected back into the lens without leaving it to reach the tissue. Light eventually reaches the inner surface of lens nearer to the light sources and leaves towards the light detectors. In other words, that selective light from a certain light source reaches the lens but never leaves the lens to reach the tissue, therefore, all the reflectance characteristics collected are related to the change in characteristics of the lens due to temperature/pressure fluctuations of the surrounding tissue.

As shown in FIG. 6F, in one or more embodiments, multiple dedicated lenses 603 may be used with light sources. For example, multiple lenses 603 may be included in a cap 104, as part of a larger lens that includes various lens portions, or positioned otherwise. In some embodiments, the multiple lenses 603 may be coupled with optical fibers that are coupled with one or more light sources (thereby dedicated). Accordingly, the characteristics of the emitted light (refraction, radiance, direction, focus, wavelengths, phase, etc.) may be enhanced or affected by each corresponding lens.

Figure 6G:
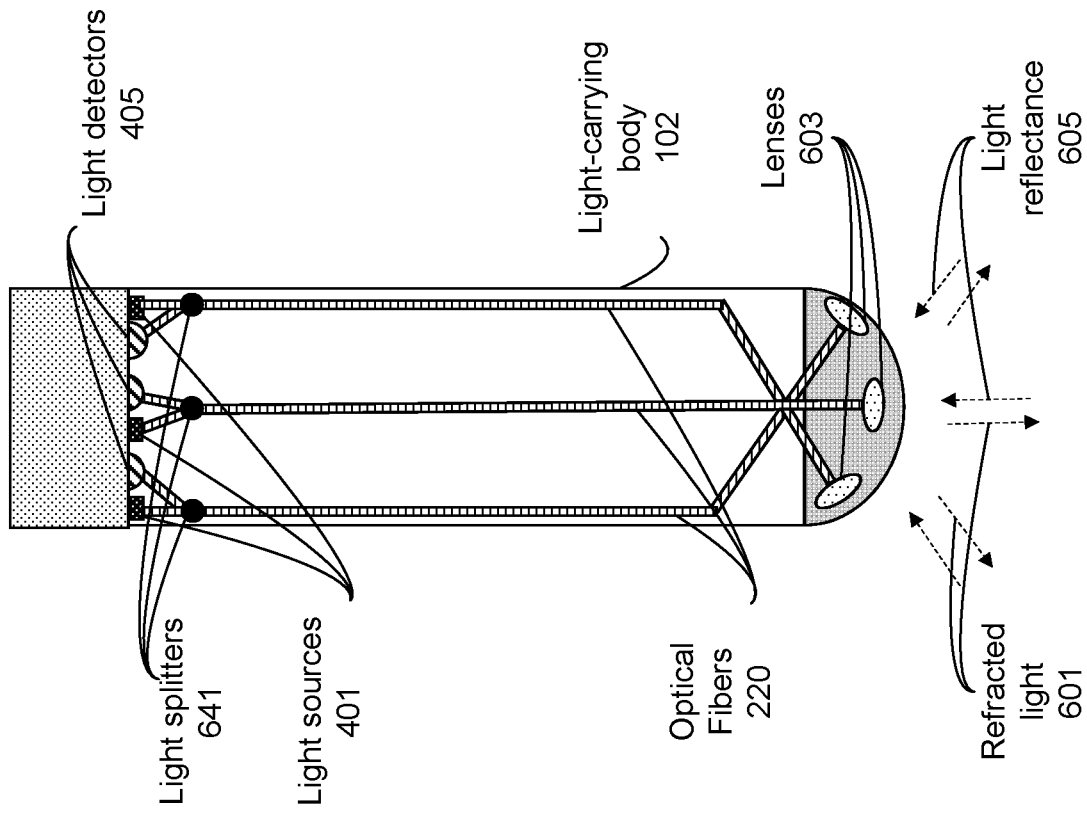

As shown in FIG. 6G, in one or more embodiments, light splitters may be used in conjunction with multiple dedicated lenses. Accordingly, advantages afforded by light splitters may be combined with those of multiple dedicated lenses. It should be understood that embodiments of the invention support other combinations. For example, light-blocking boxes may also be used with light splitters and/or multiple dedicated lenses. In another example, both the light sources and the light detectors may be optically insulated by one or more light-blocking boxes while coupled with pass-through optical fibers.

FIG. 7A shows a light-based medical device 700 with a flexible medical apparatus 750, in accordance with one or more embodiments. Examples of flexible medical apparatuses include, but are not limited to, tubes, catheters, cannulas, or the like.

The embodiments of the device 700 depicted in FIGS. 7A-7B may be the same or similar to the embodiments of the devices discussed herein (e.g., with reference to any of FIGS. 1A-1B, 2A-2C, 3A, 3E-3F, 4A-4B, and so on). One or more embodiments of the device 700, like those discussed herein, may be included in the flexible apparatus 750. For example, the lens 103 and/or cap 104 of the device 700 may be located at an insertion end of the flexible apparatus 750.

In some embodiments, the remaining components of the device 700 may also be substantially located at an insertion end of the flexible apparatus 750. In such embodiments, the device 700 may receive power via wires. Further, the device 700 may communicate with external devices (e.g., external device 760) via wires, via a wireless connection, and/or optical fibers.

In some embodiments, the remaining components of the device 700 may be substantially located at an external end of the flexible apparatus 750. For example, light sources, light detectors, a base, a controller module, an indicator, and/or a communication module may be located at the external end of the flexible apparatus 750. Such remaining components may be coupled with the lens 103 and/or cap 104 via optical fibers that extend the length of the flexible apparatus 750.

In some embodiments, the light-carrying body is substantially flexible to flex with the flexible apparatus 750. In other embodiments, the device 700 does not include a light-carrying body, but instead relies on light transmission via optical fibers.

In one or more embodiments, the device 700 communicates with an external device 760. Examples of external devices include, but are not limited to, computers, laptops, tablets, smart phones, smart TVs, wearable devices, cloud software platforms, and so on. The external device 760 may be, or work in conjunction with, the indicator of the device 700. For example, the external device 760 may provide feedback about the tissue (e.g., the type(s) of tissue, guidance advice, and so on). The external device 760 may include a remote module that performs, or aids in the performance of (e.g., in conjunction with a controller module of the device 700), the media analysis (e.g., analysis of surrounding tissue).

In one or more embodiments, the device 700 may be used to notify the user when the device 700 or relevant portion of the apparatus 750 has arrived at a target area. As a non-limiting example, a balloon catheter may be equipped with the device 700 targeting plaque during angioplasty arrives at the proper location, the user can be notified to perform an action. Non-limiting examples of actions can include pumping a balloon, placing a stent, injecting a drug, collecting a biopsy sample, and the like. Importantly the described action can be performed, with or without removal of the device 700, based on the application and design. In another example, a laparoscope may be equipped with the device 700 to aid in minimally invasive surgical procedures. In such embodiments, in addition to the utilities provided by laparoscope, the implemented device 700 can use light and reflectance analysis to provide feedback regarding the type of the surrounding and deeper tissue that is not visible or blocked.

In some embodiments, a rear or base end of the device 700 is connected to a cable/wire that extends back from inside the catheter and/or tube. This cable can be used to transfer signal and/or for removal of the device 700 (e.g., after the tip of the flexible catheter/tube reaches the targeted area). In some embodiments, after arrival at the targeted area, the device 700 can be removed by the user by use of the cable that is attached to the device, leaving the flexible apparatus 750 intact with its tip at the targeted area. The removal of the device 700 can be performed before, after, or during deployment of balloon/stent etc.

In one or more embodiments, the device 700 may be used in conjunction with medical tools that are intended for insertion in airways, such as of tubes into the trachea or lungs. For example, medical tools such as needles (such as that discussed with respect to FIGS. 1A-2D) or the flexible apparatus 750. The light radiating and collecting portions of the device 700 (e.g., the lens, cap, and/or optical fiber ends) may be positioned near a sharp tip of the tool that acts to pierce. When the light radiating and collecting portions enter an airway, the change in media is determined by the device 700 and communicated to the user. Accordingly, the user will know when to remove certain portions of the medical tools while leaving a tube remaining.

In such embodiment, the tube can be made at least in part by a double layer polymer with an attached polymer balloon that can be inflated to keep the insertion in place within the airway, allowing for easier removal of the device 700. The polymer tube may contain a gas channel that can transfer injected gas to inflate the balloon following the insertion into the airway.

In one or more embodiments, the device 700 communicates with the external device 760 via a communication module. The communication may be via a wired (e.g., FIG. 7A) or wireless (e.g., FIG. 7B) medium.

Figure 8B:
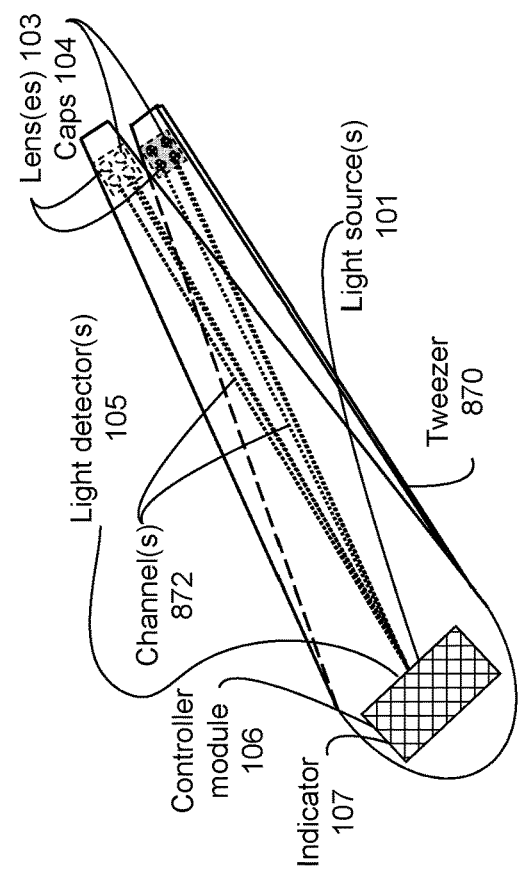
FIGS. 8A-8C show a light-based medical device and a medical tool, in accordance with one or more embodiments.
Figure 8A:
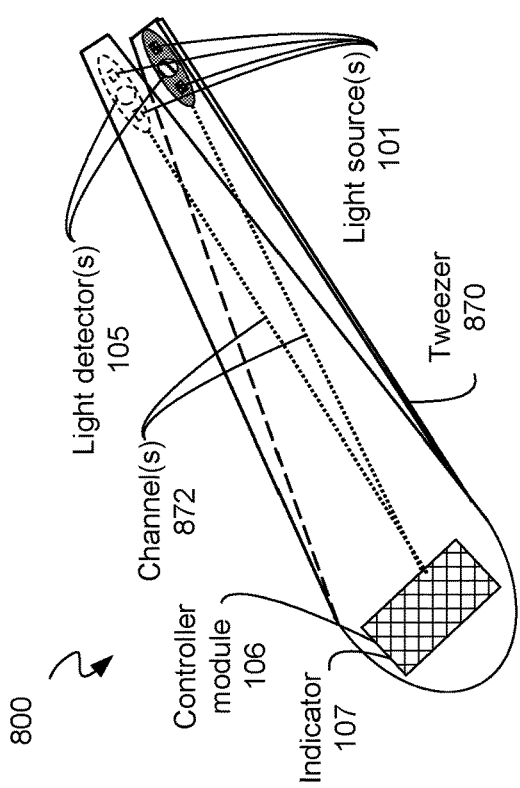
Figure 8C:
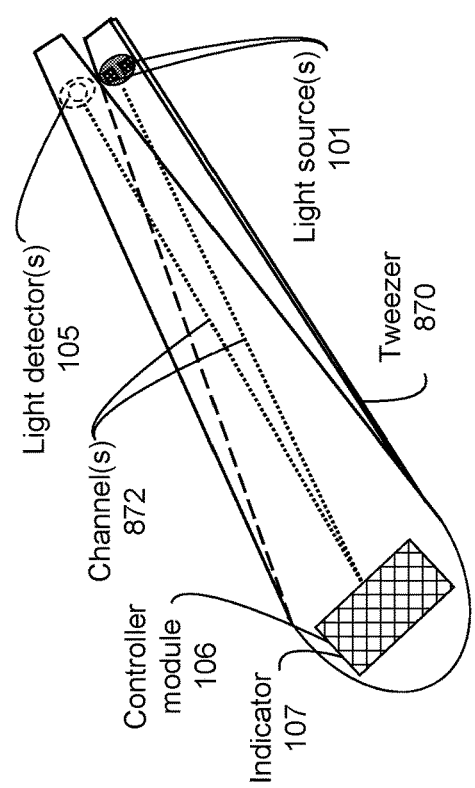

FIGS. 8A-8C show a light-based medical device 800 in conjunction with a medical tool, in accordance with one or more embodiments. It should be understood that the example of surgical tweezers 870 in FIGS. 8A-8C is simply discussed with respect to the medical device for illustrative purposes only, and that embodiments apply to any other apparatus. For example, other apparatuses that function similarly to forceps, tongs, pliers, clamps, or function to grasp or close around a specific tissue or foreign object. Further, it should be understood that various aspects, concepts, and features discussed with reference to FIGS. 8A-8C (or any other figures for that matter) may be applicable to the embodiments discussed with reference to the other figures.

Referring to FIG. 8A, in one or more embodiments, the device 800 includes one or more light sources 101 and one or more light detectors 105 located at the tip(s) of the tweezers 870 arms. In some embodiments, the light source(s) 101 and light detector(s) 105 are located on the inner side of one tip or both tips. As a result, light emitted by the light source(s) 101 can reflect off of target tissue located between the tips and thereby back toward the light detector(s) 105. Accordingly, an analysis of the target tissue can be performed based on the reflectance. In some embodiments, a light source 101 may emit light that at least partially passes through the target tissue, where the pass-through light is measured by the light detector 105 on the opposite arm. Based on characteristics of the pass-through light, an analysis of the target tissue can be performed.

In one or more embodiments, the device 800 includes one or more lenses and/or caps. For example, the lenses may be positioned over the light sources 101 to affect light radiance characteristics and/or over the light detectors 105 to affect reflectance characteristics. In another example, the caps may be positioned over the light sources 101 and/or light detectors 105 to provide a transparent seal. In yet another example, the caps may be positioned over some of the light sources 101 and/or light detectors 105, and not some of the other light sources 101 and/or light detectors 105 (so that differences in measurements can be used in the analysis).

In one or more embodiments, the tip(s) of the tweezers 870 include a cavity where components of the device 800 may be located. As a result, components like the light source(s) 101, light detector(s) 105, and/or lens(es) may be located inside the cavity and thereby set back from the surface of the tweezers 870. In some embodiments, the cap(s) may provide a substantially continuous and flush external surface with the surface of the tweezers 870.

In one or more embodiments, the device 800 includes one or more channels 872. The channel(s) 872 may extend along one or both arms of the tweezers 870. The channel(s) 872 may be operable to carry optical and/or electrical signals. For example, the channel(s) 872 may communicatively couple the controller module 106 with the light source(s) 101 and light detector(s) 105. The controller module 106 may be communicatively coupled with the indicator 107 or the communication module 108 (not shown).

In some embodiments, a tunnel or a trench in the body of the tool may extend along the tool for housing and insulating the channel(s) 872. For example, the channel(s) 872 may be set back into a trench that extends from the light source(s) 101 and light detector(s) 105 to the controller module 106. The trench may be sealed such that a flush and/or continuous tool surface is maintained. In another example, the channel(s) 872 may run along a tunnel or hollow portion that extends from the light source(s) 101 and light detector(s) 105 to the controller module 106.

In some embodiments (not shown), the controller module 106 is miniaturized and placed next to the light source(s) 101 and light detector(s) 105 at the tip of one or both arms of the medical tool 870. In such embodiments, the controller module 106 can be connected to the indicator 107 with the use of channels 872 to carry signals, or it can be coupled with the indicator 107 wirelessly (in such case there may not be any channels 872 within the body of the medical tool 870).

In some embodiments, the communication module 108 is miniaturized and located proximately to the light source(s) 101 and light detector(s) 105. In this case, the communication module can communicate with a remote indicator and controller module (e.g., a laptop, display, PC, and so on).

In some embodiments, both the communication module 108 and the controller module 106 are miniaturized and located proximately to the light source(s) 101 and the light detector(s) 105.

In some embodiments, the combination of light source(s), light detector(s), communicator module, and controller module can be located behind a lens and/or cap to create a stand-alone miniaturized insertable device that can be placed inside cavities accommodated at the tip of the arms of the tool. In such cases, there may be no need to accommodate channels 872 or trenches in the medical tool 800.

It should be appreciated that light sources can be chosen to have a certain wavelength of emission and light detectors can be chosen to have certain wavelength windows of sensitivity.

It should be appreciated that such miniaturized devices can be chosen and placed inside the cavities at the tip of the medical tool based on the application and targeted tissue. As a non-limiting example (not shown), when particles of shattered glass are being removed from inside tissue, the practitioner can choose and insert two distinctly designed miniaturized devices with certain serial numbers for example (e.g., A-01 and B-01) into the cavities of both arms. Devices designed to detect and report closing in around glass. They may or may not be identical, meaning they may comprise of different light source(s) and/or light detector(s) and/or lenses/caps. In such cases, the serial number of the devices used (A-01 and B-01 in this example) are inserted into the remote external module. The external module can then detect the type of devices being used and therefore link the collected data from both devices and merge information (for example, pass-through light and reflected light from both devices from the other or the same device) for analysis.

Referring to FIG. 8B, in one or more embodiments, the device 800 includes one or more light sources 101 and one or more light detectors 105 located at a location away from where the lens(es) 103 and/or cap(s) 104 radiate or receive light. For example, the lenses and/or caps may be located at the tip(s) of the tweezers 870 arms. Meanwhile, light source(s) 101 and light detector(s) 105 may be located nearer the base of the tweezers 870 (e.g., proximate to the controller module 106). The channel(s) 872 may be or contain optical fibers operable to carry light between the light source(s) 101/light detector(s) 105, and the lens(es) 103/cap(s) 104.

Referring to FIG. 8C, in one or more embodiments, the device 800 includes one or more light sources 101 and one or more light detectors 105 located on opposing tool arms. For example, a light source 101 may be located on the inside of one arm of the tweezers 870 while a light detector 105 is located on the inside of the opposite arm. The light source 101 may emit light that at least partially passes through the target tissue, where the pass-through light is measured by the light detector 105 on the opposite arm. Based on characteristics of the pass-through light, an analysis of the target tissue can be performed. For example, non-limiting biomarkers and analytes, for example SpO2 (aka oxygen saturation, a measure of the amount of oxygen-carrying to not carrying hemoglobin in the blood), density, temperature, and so on can be measured. In another example, foreign objects can be targeted, for example, for removal of metal, wood, or glass shards inside tissue.

It should be understood that multiple light sources 101 and/or light detectors 105 may be located on each arm. Accordingly, in one embodiment, a light source on one arm may emit and the reflectance/pass-through light is measured by light detector(s) 105 placed both on the same arm and/or on the opposite arms. Similarly, then a light source on the opposite arm may emit and the reflectance/pass-through light is measured by light detector(s) 105 placed both on the same arm and/or on the opposite arm. In another embodiment, multiple light sources 101 with different light characteristics (either all on the same side or opposing sides) may emit in combinations, and their reflectance/pass-through light is measured by light detector(s) 105 that are sensitive to a select range of emission wavelengths, on the same and opposite arms, to further increase the resolution of the target tissue analysis.

In yet another embodiment, the medical tool 870 can have multiple devices 800 on both arms, or multiple lenses 103 or caps 104 on either arm facing different directions. For example (not shown), on either arm there may be a lens that faces towards the other arm and to the inside of the medical tool 870 to determine the type of tissue it is closing around. In addition, there may be another lens at the tip of the arm that faces the trajectory of the insertion of the medical tool 870. These lenses can be a part of the same device 800 or can be from different devices. In such configurations, the device(s) 800 can give feedback on both the insertion/placement of the device tip on the tissue, the trajectory of insertion and the tissue the tool is closing around. As an example, when a metal shard is deeply embedded inside muscle tissue, such a configuration on the devices 800 placed in medical tool 870 can help the practitioner guide the tool 870 (e.g., tweezers) into the tissue and towards the trajectory of the metal shard, upon arrival to the metal shard, the feedback from the devices 800 at the tip of tool and facing towards the insertion direction notify the user to open the arms and close around the foreign object. As arms close around the foreign object (in this example the metal shard) the devices 800 facing towards the inside of the arms detect light characteristic changes and can provide confirmation or feedback with respect to clamping around the targeted object.

It should be understood that concepts discussed herein with respect to other embodiments may apply to those related to FIGS. 8A-8C. For example, a user may be able to specify information related to the procedure to aid the controller module 106 in the analysis and/or feedback. For example, the user may indicate a target region or tissue type. With such information, the controller module 106 analysis can be supplemented when making determinations about the current or proximate tissue type (e.g., if the target tissue type has been encountered, etc.).

Figure 9:
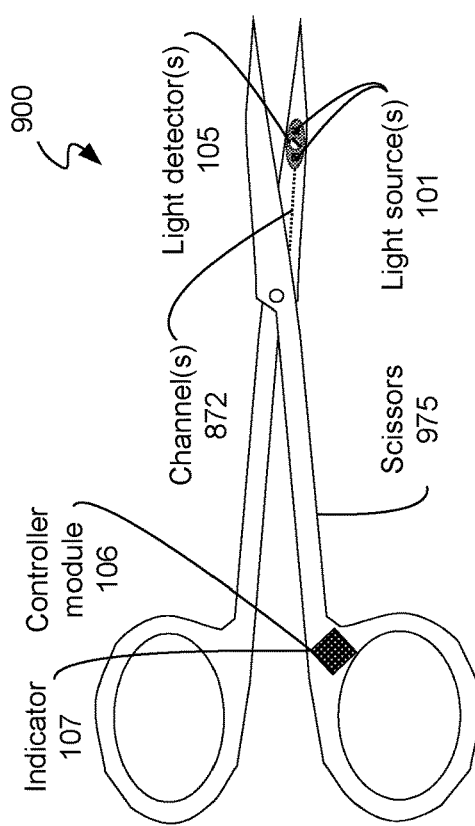
FIG. 9 shows a light-based medical device and a medical tool, in accordance with one or more embodiments.

FIG. 9 show a light-based medical device 900 in conjunction with a medical tool, in accordance with one or more embodiments. It should be understood that the example of a pair of surgical scissors 975 in FIG. 9 is simply discussed with respect to the medical device for illustrative purposes only, and that embodiments apply to any other apparatus.

For example, other apparatuses that function similarly to shearing tools. Further, it should be understood that various aspects, concepts, and features discussed with reference to FIG. 9 (or any other figures for that matter) may be applicable to the embodiments discussed with reference to the other figures.

In one or more embodiments, the device 900 includes one or more light sources 101 and one or more light detectors 105 located on the inner side of the scissors 975 blade(s). In some embodiments, the light source(s) 101 and light detector(s) 105 are located on the inner side of one blade or both blades. As a result, light emitted by the light source(s) 101 can reflect off of target tissue and thereby back toward the light detector(s) 105. Accordingly, an analysis of the target tissue can be performed based on the reflectance.

In one or more embodiments, the device 900 includes one or more light sources 101 and one or more light detectors 105 located on the blade edge of the scissors 975, similarly to the embodiments of the blade 330 discussed with respect to FIGS. 3A-3G. For example, the device 900 and/or scissors 975 may include a transparent cap that provides a substantially continuous and flush external surface with the surface of the scissors 975 (e.g., including a sharp cutting edge).

Concepts discussed with respect to FIGS. 8A-8C may apply to the device discussed with respect to FIG. 9. For example, light source(s) 101 and light detector(s) 105 can be positioned on both arms, facing toward different directions including inside and trajectory of insertion, so that the device 900 can measure both reflectance and pass-through light as well as detect the tissue at the tip and upcoming tissue. In another example, the device 900 may include lenses positioned over the light sources 101 to affect light radiance characteristics and/or over the light detectors 105 to affect reflectance characteristics. In another example, the caps may be positioned over the light sources 101 and/or light detectors 105 to provide a transparent seal. In yet another example, the blades may include a cavity where components of the device 900 may be located and thereby set back from the surface of the scissors 975. In some embodiments, cap(s) may provide a substantially continuous and flush external surface with the surface of the scissors 975.

In one or more embodiments, the device 900 includes one or more channels 872. The channel(s) 872 may be operable to carry optical and/or electrical signals. For example, the channel(s) 872 may communicatively couple the controller module 106 with the light source(s) 101 and light detector(s) 105. The controller module 106 may be communicatively coupled with the indicator 107 or the communication module 108 (not shown).

In some embodiments, a tunnel or a trench in the body of the tool may extend along the tool for housing and insulating the channel(s) 872. For example, the channel(s) 872 may be set back into a trench that extends from the light source(s) 101 and light detector(s) 105 to the controller module 106. The trench may be sealed such that a flush and/or continuous tool surface is maintained.

Similarly to the concepts discussed with respect to FIG. 8B, in one or more embodiments, the device 900 includes one or more light sources 101 and one or more light detectors 105 located at a location away from where the lens(es) 103 and/or cap(s) 104 radiate or receive light. For example, the lenses and/or caps may be located on the blade(s) of the scissors 975. Meanwhile, light source(s) 101 and light detector(s) 105 may be located nearer the handles of the scissors 975 (e.g., proximate to the controller module 106). The channel(s) 872 may be or contain optical fibers operable to carry light between the light source(s) 101/light detector(s) 105, and the lens(es)/cap(s).

Similar to what was described with respect to device 800, device 900 can also be miniaturized to fit into cavities implemented inside the arms of the tool 975. In such cases, a practitioner can choose and replace the devices 800 used in either arms based on the application.

It should be understood that while specific medical implements/tools are discussed with reference to various figures, those implements/tools are simply discussed for illustrative purposes and the device may be used with various other types of medical implements/tools. Further, it should be understood that various aspects, concepts, and features discussed with reference to any figure may be applicable to the embodiments of the device discussed with reference to the other figures. If the discussion for a particular embodiment or figure doesn't mention an aspect/concept/feature while another does, that aspect/concept/feature may still apply to the particular embodiment. For example, if a flexible light-carrying body was not explicitly discussed with respect to FIGS. 6A-6G, the discussion of a flexible light-carrying body with respect to FIGS. 7A-7B may apply to the device discussed in reference to FIGS. 6A-6G. Meanwhile, if a light-blocking box was not explicitly discussed with respect to FIGS. 7A-7B, the discussion of a light-blocking box with respect to FIGS. 6A-6G may apply to the device discussed in reference to FIGS. 7A-7B.

While the invention has been described with respect to a limited number of embodiments, those skilled in the art, having benefit of this disclosure, will appreciate that other embodiments may be devised that do not depart from the scope of the invention as disclosed herein.

It is understood that a "set" can include one or more elements. It is also understood that a "subset" of the set may be a set of which all the elements are contained in the set. In other words, the subset can include fewer elements than the set or all the elements of the set (i.e., the subset can be the same as the set).

What is claimed is:

1. A light-based device, comprising:
   a light-carrying body operable to be located inside of a medical tool, wherein the light-carrying body includes a cylindrically-shaped, integral and continuous, and optically reflective inside surface;
   a light source located inside and at a base end of the light-carrying body;
   a light detector located inside and at the base end of the light-carrying body and located substantially adjacent to the light source;
   a lens located at a probe end of the light-carrying body distal from the base end, wherein the lens is at least semi-transparent;
   a first light-carrying channel coupled with the light source, wherein the first light-carrying channel:
   extends along the light-carrying body to the lens, and
   is operable to carry light emitted from the light source; and
   a second light-carrying channel coupled with the light detector, wherein the second light-carrying channel:
   extends along the light-carrying body to the lens, and
   is operable to carry received light to the light detector.

2. The light-based device of claim 1, wherein the lens seals the light-carrying body at the base end.

3. The light-based device of claim 1, further comprising a cap located at the probe end of the light-carrying body, wherein the cap:
   is at least semi-transparent,
   seals the light-carrying body at the base end, and
   is shaped to be substantially continuous with the surface of the medical tool.

4. The light-based device of claim 3, wherein the cap includes a light-filtering material.

5. The light-based device of claim 4, wherein the light-filtering material is an analyte-sensitive coating.

6. The light-based device of claim 1, wherein the light detector includes a light-filtering material.

7. The light-based device of claim 1, wherein the light source includes a light-filtering material.

8. The light-based device of claim 1, wherein the light source emits light with a narrow band of wavelengths.

9. The light-based device of claim 1, wherein the lens includes a light-filtering material.

10. The light-based device of claim 9, wherein the light-filtering material is an analyte-sensitive coating.

11. The light-based device of claim 1, wherein the first light-carrying channel includes at least one optical fiber and the second light-carrying channel includes at least one optical fiber.

12. The light-based device of claim 1, further comprising:
   a light splitter joining the first and second light-carrying channels to form a joined light-carrying channel portion.

13. The light-based device of claim 1, further comprising a light-blocking box, wherein the light-blocking box:
   is operable to optically insulate the light source and light detector; and
   allows light passage to the light-carrying channels.

14. The light-based device of claim 1, further comprising:
   a plurality of light sources, wherein the light source is included in the plurality of light sources; and
   a plurality of light detectors, wherein the light detector is included in the plurality of light detectors.

15. The light-based device of claim 14, further comprising:
   a plurality of light-carrying channels, wherein:
   the first and second light-carrying channels are included in the plurality of light-carrying channels, and
   at least one of the plurality of light-carrying channels extends to a different region of the lens than another of the plurality of light-carrying channels.

16. The light-based device of claim 14, further comprising:
   a plurality of light-carrying channels, wherein:
   the first and second light-carrying channels are included in the plurality of light-carrying channels, and
   at least one of the plurality of light-carrying channels is operable to guide light toward the lens at a non-perpendicular angle with respect to the surface of the lens at the point where the lens surface and the at least one of the plurality of light-carrying channels are most proximate.

17. The light-based device of claim 14, further comprising:
   a plurality of lenses, wherein the lens is included in the plurality of lenses; and
   a plurality of light-carrying channels, wherein:
   the first and second light-carrying channels are included in the plurality of light-carrying channels, and at least one of the plurality of light-carrying channels extends to a different lens in the plurality of lenses than another of the plurality of light-carrying channels.

18. The light-based device of claim 14, further comprising a light-blocking box, wherein the light-blocking box:
is operable to optically insulate the light sources and light detectors; and
allows passage to the light-carrying channels.

19. The light-based device of claim 1, further comprising:
a plurality of light sources, wherein the light source is included in the plurality of light sources, and wherein at least one of the plurality of light sources emits light with a wavelength band different from another of the plurality of light sources.

20. The light-based device of claim 1, further comprising:
a plurality of light detectors, wherein the light detector is included in the plurality of light detectors, and wherein at least one of the plurality of light detectors measures light with a wavelength band different from another of the plurality of light detectors.

21. The light-based device of claim 1, wherein the lens includes a temperature-sensitive material.

22. The light-based device of claim 1, wherein the lens includes a pressure-sensitive material.

23. The light-based device of claim 1, wherein the lens includes a hydration-sensitive material.

24. The light-based device of claim 1, further comprising:
a plurality of lenses, wherein the lens is included in the plurality of lenses, wherein at least one lens of the plurality of lenses includes a temperature-sensitive material and at least one other lens of the plurality of lenses does not include a temperature-sensitive material.

25. The light-based device of claim 1, further comprising:
a plurality of lenses, wherein the lens is included in the plurality of lenses, wherein at least one lens of the plurality of lenses includes a pressure-sensitive material and at least one other lens of the plurality of lenses does not include a pressure-sensitive material.

26. The light-based device of claim 1, further comprising:
a plurality of lenses, wherein the lens is included in the plurality of lenses, wherein at least one lens of the plurality of lenses includes a hydration-sensitive material and at least one other lens of the plurality of lenses does not include a hydration-sensitive material.

27. The light-based device of claim 1, further comprising a controller module, wherein the controller module is:
coupled with the light source and the light detector;
operable to activate the light source and receive measurements from the light detector; and
operable to perform media analysis based on the light detector measurements.

28. The light-based device of claim 27, further comprising an indicator module, wherein the indicator module is:
operable to display feedback information corresponding to the media analysis performed by the controller module.

29. The light-based device of claim 1, wherein:
the light-carrying body is located inside of the medical tool, and
the medical tool comprises at least one selected from a group consisting of a needle, scalpel, catheter, cannula, tube, pair of scissors, and tweezers.

30. A light-based device, comprising:
a light-carrying body operable to be located inside of a medical tool, wherein an inside surface of the light-carrying body is cylindrically-shaped, integral and continuous, and optically reflective along the cylindrical inside surface;
a light source located inside and at a base end of the light-carrying body; and
a light detector located inside and at the base end of the light-carrying body and located substantially adjacent to the light source.

31. The light-based device of claim 30, further comprising:
a plurality of light sources, wherein the light source is included in the plurality of light sources; and
a plurality of light detectors, wherein the light detector is included in the plurality of light detectors.

32. The light-based device of claim 30, wherein the light detector includes a light-filtering material.

33. The light-based device of claim 30, wherein the light source includes a light-filtering material.

34. The light-based device of claim 30, wherein the light source emits light with a narrow band of wavelengths.

35. The light-based device of claim 30, further comprising a cap located at a probe end of the light-carrying body distal from the base end, wherein the cap:
is at least semi-transparent, and
seals the light-carrying body at the end.

36. The light-based device of claim 35, wherein the cap is shaped to be substantially continuous with the surface of the medical tool.

37. The light-based device of claim 35, wherein the cap includes a light-filtering material.

38. The light-based device of claim 37 wherein the light-filtering material includes an analyte-sensitive coating.

39. The light-based device of claim 30, further comprising a lens located at a probe end of the light-carrying body distal from the base end, wherein the lens is at least semi-transparent.

40. The light-based device of claim 39, further comprising:
a plurality of lenses, wherein the lens is included in the plurality of lenses, wherein at least one of the plurality of lenses is located longitudinally with respect to another of the plurality of lenses.

41. The light-based device of claim 39, further comprising:
a plurality of lenses, wherein the lens is included in the plurality of lenses, wherein at least one of the plurality of lenses is located radially with respect to another of the plurality of lenses.

42. The light-based device of claim 39 wherein the lens includes a light-filtering material.

43. The light-based device of claim 42 wherein the light-filtering material includes an analyte-sensitive coating.

44. The light-based device of claim 30, further comprising a lens located at a probe end of the light-carrying body distal from the base end, wherein the lens is at least semi-transparent and wherein the lens includes a temperature-sensitive material.

45. The light-based device of claim 30, further comprising a lens located at a probe end of the light-carrying body distal from the base end, wherein the lens is at least semi-transparent and wherein the lens includes a pressure-sensitive material.

46. The light-based device of claim 30, further comprising a lens located at a probe end of the light-carrying body distal from the base end, wherein the lens is at least semi-transparent and wherein the lens includes a hydration-sensitive material.

47. The light-based device of claim 30, further comprising:
a plurality of lenses located at a probe end of the light-carrying body distal from the base end, wherein at least one lens of the plurality of lenses includes a temperature-sensitive material and at least one other lens of the plurality of lenses does not include a temperature-sensitive material.

48. The light-based device of claim 30, further comprising:
a plurality of lenses located at a probe end of the light-carrying body distal from the base end, wherein at least one lens of the plurality of lenses includes a pressure-sensitive material and at least one other lens of the plurality of lenses does not include a pressure-sensitive material.

49. The light-based device of claim 30, further comprising:
a plurality of lenses located at a probe end of the light-carrying body distal from the base end, wherein at least one lens of the plurality of lenses includes a hydration-sensitive material and at least one other lens of the plurality of lenses does not include a hydration-sensitive material.

50. The light-based device of claim 30, further comprising:
a plurality of light sources, wherein the light source is included in the plurality of light sources, and wherein at least one of the plurality of light sources emits light with a wavelength band different from another of the plurality of light sources.

51. The light-based device of claim 30, further comprising:
a plurality of light detectors, wherein the light detector is included in the plurality of light detectors, and wherein at least one of the plurality of light detectors measures light with a wavelength band different from another of the plurality of light detectors.

52. The light-based device of claim 30, further comprising a controller module, wherein the controller module is:
coupled with the light source and the light detector;
operable to activate the light source and receive measurements from the light detector; and
operable to perform media analysis based on the light detector measurements.

53. The light-based device of claim 52, further comprising an indicator module, wherein the indicator module is:
operable to display feedback information corresponding to the media analysis performed by the controller module.

54. The light-based device of claim 30, wherein:
the light-carrying body is located inside of the medical tool, and
the medical tool comprises at least one selected from a group consisting of a needle, scalpel, catheter, cannula, tube, pair of scissors, and tweezers.

55. A light-based device, comprising:
a light-carrying body, wherein the light-carrying body includes a cylindrically-shaped, integral and continuous, and optically reflective inside surface;
a light source located inside of the light-carrying body operable to emit light into an environment, wherein the light is emitted with known wavelengths and intensities;
a light detector located inside of the light-carrying body operable to measure characteristics of light received from the environment;
a lens operable to guide the emitted light into the environment and guide the received light from the environment;
a set of optical fibers located inside of the light-carrying body and coupled with the light source and the light detector, wherein the set of optical fibers:
extends to the lens, and
is operable to carry the light emitted from the light source and the received light to the light detector.

56. The light-based device of claim 55, wherein the lens is temperature sensitive.

57. The light-based device of claim 55, wherein the lens is pressure sensitive.

58. The light-based device of claim 55, wherein the lens is hydration sensitive.

59. The light-based device of claim 55, wherein the light detector is operable to measure a predetermined range of light wavelengths.

60. The light-based device of claim 55, further comprising:
a plurality of light sources, wherein the light source is included in the plurality of light sources, and wherein at least one of the plurality of light sources emits light with a wavelength band different from another of the plurality of light sources.

61. The light-based device of claim 55, further comprising:
a plurality of light detectors, wherein the light detector is included in the plurality of light detectors, and wherein at least one of the plurality of light detectors measures light with a wavelength band different from another of the plurality of light detectors.

62. The light-based device of claim 55, further comprising a controller module, wherein the controller module is operable to: activate the light source, receive measurements from the light detector, and perform media analysis based on the light detector measurements.

63. The light-based device of claim 55, further comprising an indicator module, wherein the indicator module is operable to display feedback information corresponding to the media analysis performed by the controller module.

64. The light-based device of 55, wherein the set of optical fibers are located inside of the medical tool, and the medical tool comprises at least one selected from a group consisting of a needle, scalpel, catheter, cannula, tube, pair of scissors, and tweezers.

* * * * *